United States Patent [19]

Bunnell

[11] 4,223,133

[45] Sep. 16, 1980

[54] CEPHALOSPORIN REDUCTION PROCESS

[75] Inventor: Charles A. Bunnell, Lafayette, Ind.

[73] Assignee: Eli Lilly and Company, Indianapolis, Ind.

[21] Appl. No.: 8,645

[22] Filed: Feb. 1, 1979

[51] Int. Cl.$^2$ .......................................... C07D 501/04
[52] U.S. Cl. ....................................... 544/16; 544/21; 544/22; 424/246
[58] Field of Search ............................. 544/16, 21, 22

[56] References Cited

U.S. PATENT DOCUMENTS

| | | | |
|---|---|---|---|
| 3,641,014 | 2/1972 | Murphy et al. | 260/242 C |
| 3,922,268 | 11/1975 | Murphy et al. | 544/16 |
| 4,044,002 | 9/1977 | Hatfield | 544/16 |
| 4,115,643 | 9/1978 | Kukolja et al. | 544/16 |

OTHER PUBLICATIONS

Drabowicz et al., Organic Preparations and Procedures Int. 9(2), 63–83 (1977).
Coe et al., J. Chem. Soc., 1954, pp. 2281–2287.

*Primary Examiner*—Nicholas S. Rizzo
*Attorney, Agent, or Firm*—Steven R. Lammert; Arthur R. Whale

[57] ABSTRACT

Cephalosporin sulfoxides are reduced to the corresponding cephalosporins in the presence of a halogen scavenger with triaryl phosphite-halogen complexes derived from the kinetically controlled reaction of selected triaryl phosphites and chlorine or bromine.

77 Claims, No Drawings

CEPHALOSPORIN REDUCTION PROCESS

BACKGROUND OF THE INVENTION

Cephalosporin sulfoxides are widely used intermediates in the synthesis of cephalosporin antibiotics. For example, cephalosporin sulfoxides are useful in the overall process for converting 3-methyl-3-cephem(-desacetoxycephalosporins) compounds to 3-substituted-methyl-3-cephem antibiotic compounds. This functionalization of 3-methyl-3-cephem compounds proceeds via the isomerization of the 3-methyl-3-cephem to a 3-methyl-2-cephem, functionalization of the activated 3-methyl group of the 2-cephem compound, for example, with bromine, followed by oxidation of the 3-substituted-methyl-2-cephem compound to the sulfoxide. Oxidation to the sulfoxide causes the isomerization of the 2-cephem to the 3-cephem product. The isomerization of 3-halomethyl-2-cephem compounds to the corresponding 3-halomethyl-3-cephem compounds is described by Murphy in U.S. Pat. No. 3,647,786, and by Webber in U.S. Pat. Nos. 3,766,177, 3,637,678, and 3,708,479.

Additional examples of uses of cephalosporin sulfoxides are the N-deformylation procedure of 7-$\beta$-formamido-3-halomethyl-3-cephem sulfoxides described by Humber in U.S. Pat. No. 3,716,533, the 3-formyl-3-cephem sulfoxides described by Webber in U.S. Pat. No. 3,674,784 and the 7-(D-2,2-dimethyl-3-nitroso-5-oxo-4-phenyl-1-imidazolidinyl)-3-bromomethyl-3-cephem-4-carboxylic acid sulfoxides described by Chaney et al. in U.S. Pat. No. 3,767,655.

Still further examples of the use of cephalosporin sulfoxides in the synthesis of cephalosporin antibiotics are the 7-acylamido-2-spirocyclopropyl cephalosporin sulfoxides described by Spry in U.S. Pat. No. 3,843,640, the 2-methylene and 2-methyl substituted cephalosporin sulfoxides described by Wright in U.S. Pat. No. 3,660,396 and the tricyclic cephalosporin sulfoxides described by Spry in U.S. Pat. No. 3,907,785. The preparation of 3-exomethylenecepham sulfoxides via azetidinone sulfinyl chlorides and Lewis acid type Friedel-Crafts catalyst is described by Kukolja in U.S. Pat. No. 4,052,387. These 3-exomethylenecepham sulfoxides are useful intermediates in the preparation of the 3-halo substituted cephalosporins described by Chauvette in U.S. Pat. No. 3,925,372 and in the synthesis of 3-methoxy-3-cephem antibiotic compounds described by Chauvette in U.S. Pat. Nos. 3,917,587 and 3,917,588. For example, an ester of a 3-exomethylenecepham sulfoxide is reduced to the corresponding 3-exomethylenecepham ester, the ester is then reacted with ozone to form the corresponding 3-hydroxy-3-cephem ester, and the 3-hydroxy ester is reacted with phosphorous trichloride to form the corresponding 3-chloro-3-cephem ester. Alternatively, the 3-hydroxy ester is reacted with diazomethane to form the corresponding 3-methoxy-3-cephem ester. Deesterification of the 3-halo and 3-methoxyesters, affords corresponding 3-halo or 3-methoxy-substituted antibiotic acid.

As noted above, cephalosporin sulfoxides are generally useful in the synthesis of cephalosporin antibiotics. Following the completion of the reactions or synthetic procedures employing the sulfoxide form of a cephalosporin, the sulfoxide function is reduced to provide the cephalosporin molecule in the reduced or sulfide state.

Prior to this invention one preferred method for reducing cephalosporin sulfoxides was that of Murphy et al., U.S. Pat. No. 3,641,014. According to this method, cephalosporin sulfoxides are reduced with (1) hydrogen and a hydrogenation catalyst, (2) stannous, ferrous, cuprous, or manganous cations, (3) dithionite, iodide, or ferrocyanide, (4) trivalent phosphorous compounds, (5) halosilanes or (6) chloromethylene iminium chlorides wherein certain of these reducing agents require the use of an activator such as acetyl chloride or phosphorous trichloride. For example, sodium dithionate is activated with acetyl chloride in the reduction. Another method for the reduction of cephalosporin sulfoxides was disclosed by Hatfield in U.S. Pat. No. 4,044,002 which describe the reduction of cephalosporin sulfoxides using acyl bromides in the presence of bromine scavengers. More recently Kukolja and Spry described the reduction/chlorination of 3-hydroxycephem sulfoxides using phosphorous trichloride, phosphorous pentachloride or phosgene in the presence of dimethylformamide.

In view of the usefulness of cephalosporin sulfoxides in the synthesis of cephalosporin antibiotics, more efficient and more economical methods for sulfoxide reduction, have been the object of extensive research efforts. It is an object of this invention to provide a process for the reduction of cephalosporin sulfoxides. More particularly this invention is directed to a process for reducing cephalosporin sulfoxides using a recently discovered class of triaryl phosphite-halogen compounds, derived from the kinetically controlled reaction of equivalent amounts of triaryl phosphites and chlorine or bromine. The triaryl phosphite-halogen reducing compounds employed the present reduction process are useful for effecting other desirable chemical modifications (halogenation) of cephalosporin compounds. It is therefore another object of the present invention to provide processes for one step reduction/halogenation conversions of C-7 acylamino cephalosporin sulfoxides to 7-amino cephalosporins or depending on the the cephalosporin starting materials and the amounts of reagents employed C-7 acylamino halogenated cephalosporins or C-7 amino halogenated cephalosporins.

SUMMARY OF THE INVENTION

According to the process of the present invention a cephalosporin sulfoxide is reacted in inert organic solvent with about 1 to about 1.3 molar equivalents of a triaryl phosphite-halogen complex, derived from the kinetically controlled reaction of a triaryl phosphite and chlorine or bromine, in the presence of a halogen scavenger to provide the corresponding cephalosporin.

The present invention is also directed to processes wherein the triaryl phosphite-halogen complex is utilized to effect multiple chemical conversions of the cephalosporin sulfoxide starting materials in one reaction mixture. In these alternate process embodiments of the present invention, with the reduction of the sulfoxide moiety there is concomitant halogenation either at C-3, if the starting material is a 3-hydroxy cephalosporin sulfoxide, at C-7 (to form the imino halide of the acylamino group), or at both positions when sufficient triaryl phosphite-halogen complex is used in the presence of a tertiary amine base. The imino halides produced from C-7 acylamino cephalosporin sulfoxides in accordance with the present process are easily cleaved by art recognized procedures via imino ether intermediates to form the corresponding C-7 amino cephalosporins.

The products formed in the present process are known antibiotic compounds or intermediates thereto.

DETAILED DESCRIPTION OF THE INVENTION

This invention is directed to a process for reducing cephalosporin sulfoxides which comprises reacting said cephalosporin sulfoxide with about 1.0 to about 1.3 equivalents of a reducing compound of the general formula

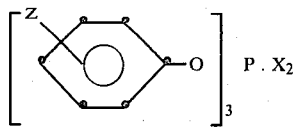

wherein X is Cl or Br, and Z is hydrogen, halo, $C_1-C_4$ alkyl, or $C_1-C_4$ alkoxy which in the kinetically controlled product of the reaction of equivalent amounts of a triaryl phosphite of the formula

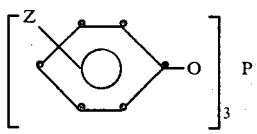

and chlorine or bromine in a substantially anhydrous inert organic solvent; in the presence of at least a molar equivalent of a halogen scavenger, more particularly a chlorine or bromine scavenger, in a substantially anhydrous inert organic solvent at a temperature of about 30° C. or below.

This process is illustrated by the following generalized reaction scheme;

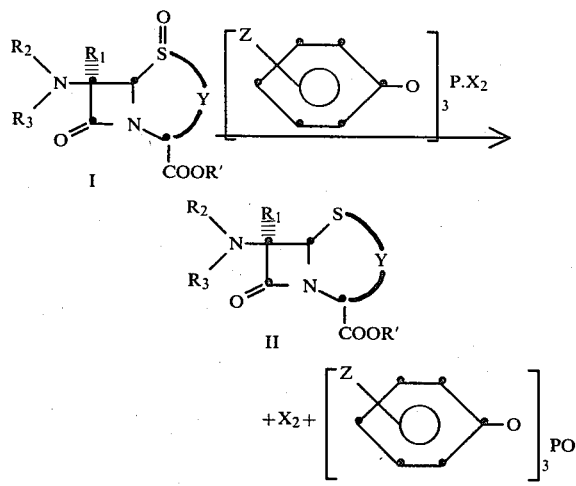

In the above formulas R' represents hydrogen or a carboxylic acid protecting group, $R_1$ represents hydrogen or methoxy, the group

represents a substituted amino group, and Y represents a divalent radical selected from the group

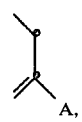         (a)

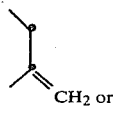         (b)

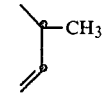         (a)

wherein A represents hydrogen or a substituent group.

The sulfoxide reduction process of this invention can be carried out on any cephalosporin sulfoxide. As discussed above, numerous cephalosporin sulfoxides have been described and are commonly employed intermediates in the synthesis of cephalosporin antibiotics.

As used herein, the term "cephalosporin sulfoxide" refers to the bicyclic compounds having a 4-membered β-lactam ring fused to a 6-membered thiazine or a dihydrothiazine ring. When in the above formula I Y is the structural moiety (a), the cephalosporin sulfoxide is alternatively named according to the cepham nomenclature system as a 3-cephem sulfoxide or 3-cephem 1-oxide. Likewise, when Y is the structural moiety (b), the cephalosporin sulfoxide is named as a cepham sulfoxide and in particular a 3-exomethylenecepham sulfoxide.

The cephalosporin sulfoxide used in the present process can have either the R or S configuration at sulfur.

The reduction process of this invention has been carried out successfully on cephalosporins bearing a free enolic hydroxy function (a 3-hydroxy-3-cephem sulfoxide). However, because of the reactivity of the triaryl phosphite-halogen complex it is preferred that cephalosporin sulfoxides bearing reactive functional groups such as hydroxy, amino or carboxy groups, be protected with one of the conventional hydroxy, amino or carboxy protecting groups prior to being employed in the present process. Of course, additional amounts of kinetic complex can be employed to compensate for the presence of reactive functional groups on the cephalosporin molecule. Free carboxylic acid groups, for example, are converted to the corresponding acid halides which are easily hydrolyzed back to the acid.

The Reducing Compound

The reducing compound used in the present process, triaryl phosphite-halogen complexes, are recently discovered compounds derived from the reaction of selected triaryl phosphites and chlorine or bromine. They are known to be useful in preparing 3-halocephalosporins from 3-hydroxycephalosporins and imino halides derived from C-6 acylamino penicillins and C-7 acylamino cephalosporins.

Triaryl phosphites of the formula

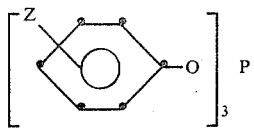

wherein Z is hydrogen, halo, $C_1$–$C_4$ alkyl or $C_1$–$C_4$ alkoxy, react with equivalent amounts of chlorine or bromine in a substantially anhydrous inert organic solvent to provide, initially, kinetically controlled products having the empirical formula

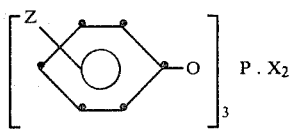

wherein Z is as defined above and X is Cl or Br.

The term "halo" in the definition of Z includes chloro, bromo or iodo. "$C_1$–$C_4$ Alkyl" includes methyl, ethyl, isopropyl, n-propyl, n-butyl, sec-butyl, tert-butyl and isobutyl. Representative "$C_1$–$C_4$ alkoxy" groups are methoxy, ethoxy, isopropoxy, tert-butoxy and n-butoxy.

The dot (.) in the general formula used to represent the kinetically controlled products employed in the present processes is used simply to designate that equivalent amounts of halogen and triaryl phosphite are combined chemically and in a way that can be distinguished from that in the thermodynamically stable derivatives which have been known in the art and which typically have been drawn without the dot [e.g. $(PhO)_3PCl_2$]. The exact molecular form of the triaryl phosphite-halogen kinetic complexes described herein has not been established definitively; however, physical-chemical data do indicate that the kinetic product is one wherein the phosphoric center aquires some cationic character. Herein the terms "kinetic compound", "kinetic complex", "triaryl phosphite-halogen complex (compound)", "kinetically controlled products" and "kinetically controlled halogenating (reducing) compounds" are used synonomously.

Suitable triaryl phosphites for the preparation of the kinetically controlled compounds used in the present process include triphenyl phosphite, tri(p-methoxyphenyl)phosphite, tri(o-chlorophenyl)phosphite, tri(p-chlorophenyl)phosphite, tri(p-tolyl)phosphite, tri(o-tolyl)phosphite, tri(m-bromophenyl)phosphite, tri(p-bromophenyl)-phosphite, tri(p-iodophenyl)phosphite, tri(p-n-propylphenyl)phosphite, tri(p-tert-butylphenyl)phosphite, tri(m-tolyl)phosphite, tri(p-isopropoxyphenyl)phosphite and the like. Triphenyl phosphite is preferred, primarily because of commercial availability.

Any of a wide variety of inert organic solvents may be employed as the medium for the preparation of the kinetically controlled compounds and for the reduction and reduction-halogenation processes described hereinbelow. By "inert organic solvent" is meant an organic solvent which under the reaction conditions of the preparation does not enter into any appreciable reaction with either the reactants or the products. Since the halogenating compounds are susceptible to reaction with protic compounds, such compounds, including water, alcohols, amines (other than tertiary), thiols, organic acids and other such protic compounds should be excluded from the reaction medium.

A substantially anhydrous aprotic organic solvent is preferred. The term "substantially anhydrous" as used in the present description means that although anhydrous organic solvents are generally preferred, trace amounts of water, such as that often found in commercially available solvents, can be tolerated. Although the kinetic products described herein will react with any water present in the solvent medium, additional amounts of reagents can easily be added to compensate for the loss due to hydrolysis. It is preferred that conventional laboratory techniques be employed to dry the solvents employed and to exclude moisture from the reaction mixtures.

Suitable solvents include hydrocarbons, both aliphatic and aromatic, including pentane, hexane, heptane, octane, cyclohexane, cyclopentane, benzene, toluene, o-, m- or p- xylene, mesitylene and the like; ethers, cyclic and acyclic such as diethyl ether, butyl ethyl ether, tetrahydrofuran, dioxane, 1,2-dimethoxyethane and the like; carboxylic acid esters such as ethyl acetate, methylformate, methyl acetate, amyl acetate, n-butyl acetate, sec-butyl acetate, methyl propionate, methyl butyrate and the like; nitriles such as acetonitrile, propionitrile, butyronitrile and the like; halogenated hydrocarbons, both aromatic and aliphatic, such as chloroform, methylene chloride, carbon tetrachloride, 1,2-dichloroethane (ethylene dichloride), 1,1,2-trichloroethane, 1,1-dibromo-2-chloroethane, 2-chloropropane, 1-chlorobutane, chlorobenzene, fluorobenzene, o-, m-, or p- chlorotoluene, o-, m-, or p- bromotoluene, dichlorobenzene and the like; and nitro compounds such as nitromethane, nitroethane, 1- or 2-nitropropane, nitrobenzene and the like.

The particular inert organic solvent employed as a medium for the preparation of the kinetically controlled triaryl phosphite-halogen compounds or as a medium for their use in the present processes is not critical, however, such solvent properties as polarity, melting or boiling point, and ease of isolation of products may be considered in selecting a most suitable solvent.

Preferred solvents for the preparation of the kinetically controlled products and for the present processes described hereinbelow are hydrocarbons, especially aromatic hydrocarbons, and halogenated hydrocarbons. Halogenated hydrocarbons other than chloroform are more preferred. Methylene chloride is most preferred.

If a compound derived from the kinetically controlled reaction of a triaryl phosphite and chlorine or bromine is allowed to stand in solution it converts or isomerizes to the corresponding thermodynamically stable compound at varying rates depending on, among other things, the nature of the triaryl phosphite, the solvent, the halogen, and the solution temperature. Experimental data has also shown that the presence of an acid (HX) or an excess of triaryl phosphite will enhance the rate of conversion of the kinetic to the thermodynamic product.

Using $^{31}P$ nuclear magnetic resonance spectroscopy the half-life of the kinetically controlled product from the reaction of triphenyl phosphite and chlorine in methylene chloride at room temperature was determined to be about 8 hours. A half-life of about 39 hours was observed for the triphenyl phosphite-bromine kinetic complex under the same conditions. As mentioned above the observed half-life (rate of conversion) for any given kinetic complex described herein can be affected by the solvent and by the presence of a hydrogen halide acid (HX) or excess triaryl phosphite. Thus, for example, a shorter half-life will be observed where the solvent for the preparation of kinetic complex has not been rigorously dried; the hydrogen halide acid produced from reaction of the kinetic complex with the moisture present in the solvent will enhance the rate of conversion to the stable form. Table I presents a summary of several properties of the kinetically controlled product and the corresponding thermodynamically controlled product of the reaction of triphenyl phosphite and chlorine.

action temperatures are in the range of about $-70°$ to about $0°$ C.

It has been found that the triaryl phosphite itself reacts to some extent with its kinetic reaction product with chlorine or bromine, effectively increasing the rate of conversion to the corresponding thermodynamic product. It is preferred, therefore, but not required, that an excess of halogen be maintained in the reaction mixture during the formation of the kinetic compounds. This can be achieved practically by adding the triaryl phosphite to a solution of an equivalent amount of the halogen or by adding the halogen and the triaryl phosphite simultaneously to a quantity of inert organic sol- Table I

|   | Kinetic product | | Thermodynamic product |
|---|---|---|---|
| 1. | $^{31}$P nmr (CH$_2$Cl$_2$) $-$ 3.7 ppm* | 1. | $^{31}$P nmr (CH$_2$Cl$_2$) $+$ 22.7 ppm* |
| 2. | $t_{\frac{1}{2}} = \cong 8$ hours at room temperature in methylene chloride | 2. | Stable at room temperature |
| 3. | ir (CH$_2$Cl$_2$) 1120–1190 (vs), 1070 (vs), 1035 (s), 1010 (vs), 990 (vs), 640 (m), 625 (m), 580 (w), 510 (s), 465 (w).** | 3. | ir (CH$_2$Cl$_2$) 1130–1210 (vs), 1065 (vs), 1035 (s), 1010 (vs), 980 (vs), 625 (vw), 590 (m), 505 (s) 460 (s).** |
| 4. | Hydrolyzes to give HCl and (PhO)$_3$PO | 4. | Hydrolyzes to give inter alia HCl, PhOH (phenol) and (PhO)$_2$PCl |
| 5. | Reacts with n-BuOH to give HCl, n-BuCl and PhO$_3$PO | 5. | Reacts with n-BuOH to give HCl, PhOH (phenol), n-BuCl and (PhO)$_a$-(BuO)$_b$ POCl$_c$ wherein a,b,c, = 0, 1, 2 or 3 and a+b+c = 3 |

*Relative to $^{31}$P of H$_3$PO$_4$; (+) indicates upfield shift; (−) indicates downfield shift
**vs = very strong, s = strong, m = medium, w = weak The term kinetically controlled product is a term of art which when used in reference to reactions yielding two (or more) products, refers to the product formed faster, regardless of its thermodynamic stability. If such a reaction is stopped well before the products achieve thermodynamic equilibrium, the reaction is said to be kinetically controlled since more of the faster formed product will be present. In some cases, including the reaction of triaryl phosphites with chlorine or bromine, the rate of formation of the kinetic product and the rate of thermodynamic equilibrium is such that the kinetically controlled product can be prepared and utilized before any significant amount of the kinetically controlled product equilibrates or isomerizes to the thermodynamically stable product.

To maximize the production and stability of the kinetically controlled product, reaction conditions are selected so as to minimize the potential for thermodynamic equilibrium of the initial product of the reaction. Most simply conditions for kinetic control are achieved both by lowering the reaction temperature and the temperature of the kinetic product after it is formed, and by minimizing the time allowed for thermodynamic equilibrium, such as, by utilizing the kinetic product in a subsequent reaction shortly after it has been prepared.

Typically the reactants, a triaryl phosphite and chlorine or bromine, are combined in a substantially anhydrous inert organic solvent at a temperature below about $30°$ C. Although the kinetically controlled products are formed at higher temperature, such conditions favor the formation of the thermodynamically controlled products. Preferably the triaryl phosphite-halogen compounds are prepared at temperatures at or below about $30°$ C. Minimum reaction temperature are, of course, determined by the freezing point of the solvent employed for the preparation. Most preferred revent at the desired temperature. The co-addition of reagents is conducted at such a rate that the color of the halogen persists in the reaction mixture until the last drop of triaryl phosphite discharges the color. Alternatively excess halogen can be discharged using known halogen scavengers such as acetylenes, or olefins including alkenes, dienes, cycloalkenes, or bicycloalkenes. A preferred scavenger is a $C_2$ to $C_6$ alkene, for example, ethylene, propylene, butylene, or amylene.

The kinetically controlled triaryl phosphite-halogen complexes used in the process of the present invention are stabilized in solution by the addition of about 10 to about 100 mole percent of a tertiary amine base having a p$K_b$ value of about 6 to about 10. If, for example, about 50 mole percent of pyridine is added to a solution of the kinetically controlled product of the reaction of triphenyl phosphite and chlorine in methylene chloride, only trace amounts of the thermodynamic equilibrium product can be detected by $^{31}$P nmr, even after prolonged periods at room temperature. The tertiary amine base can be added to a solution of the freshly prepared triaryl phosphite-halogen complex or, optionally, it can be employed in the reaction mixture of the triaryl phosphite and halogen to produce a stabilized solution of the kinetically controlled product used in the present invention.

The Halogen Scavenger

As the reduction process of the present invention proceeds, chlorine or bromine (depending on the triaryl phosphite-halogen complex employed) is produced as a by-product. In order to prevent undesirable side reactions between the halogen by-product and the cephalosporin product, a halogen scavenger is used in the reaction mixture to react with or inactivate the chlorine or bromine as it is formed. The term "halogen scavenger" as used herein in the description of the present invention refers to organic substances which react readily with chlorine or bromine and which do not react with the triaryl phosphite-halogen complex used as a reducing agent in the present process. Representative of halogen scavengers which can be employed in the present process are alkenes, cycloalkenes, bicycloalkenes, dienes, cyclodienes, bicyclodienes, alkynes or substituted aromatic hydrocarbons which readily undergo electrophilic substitution with bromine or chlorine, for example mono hydric phenols and the ethers and esters of monohydric and polyhydric phenols. Examples of such halogen scavengers include the $C_2$ to $C_{10}$ alkenes, such as ethylene, propylene, butene-1, butene-2, isobutylene, pentene-1, penten-2, 2-methylbutene-1, 3-methylbutene-1, hexene-1, heptene-1, octene-1, the isomeric nonenes, and the like; cycloalkenes having from 5 to 8 ring carbon atoms such as cyclopentene, cyclohexene, cycloheptene, and cyclooctene; $C_4$–$C_8$ dienes and cyclodienes having from 5–8 ring carbon atoms, for example, pentadiene, hexadiene, heptadiene, cyclopentadiene, cyclohexadiene, cyclooctadiene, 2,3-dimethylbutadiene-1,3-isoprene, and the like; alkynes having from 2–6 carbon atoms, such as acetylene, methylacetylene, ethylacetylene, dimethylacetylene, pentyne-1, pentyne-2, the isomeric hexynes, 3-methylbutyne-1, 3,3-dimethylbutyne-1, and like acetylenes wherein the acetylenic bond will rapidly add chlorine or bromine (phenylacetylene was found to be an unsatisfactory chlorine scavenger); bicyclic unsaturated hydrocarbons such a camphene and pinene; and phenol ethers, substituted phenol ethers, and lower alkanoyl phenol esters represented by the formula

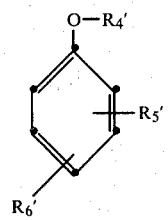

wherein $R_4'$ is $C_1$–$C_4$ alkyl or $C_2$–$C_5$ alkanoyl, $R_5'$ and $R_6'$ are independently hydrogen, $C_1$–$C_4$ alkoxy, $C_2$–$C_5$ alkanoyl, or $C_1$–$C_4$ alkyl. Examples of such derivatives include the hydroquinone monomethyl ether, hydroquinone dimethyl ether, anisole, phenetole, m-dimethoxybenzene, veratrole, phenyl propionate, phenyl acetate, resorcinol diacetate, and like phenol ethers and esters which react readily with chlorine or bromine.

Preferred halogen scavengers are $C_2$–$C_6$ alkenes, for example, ethylene, propylene, butylene amylene, cyclopentene or cyclohexene.

Since theoretically at least 1 molar equivalent of halogen is produced for each equivalent of sulfoxide reduced in the present process, at least a molar equivalent amount of halogen scavenger is employed in the cephalosporin sulfoxide reduction process for each equivalent of cephalosporin sulfoxide starting material. Typically about 1 to about 3 molar equivalents of halogen scavenger is used for each equivalent of starting material; however, larger amounts of halogen scavenger can be employed without affecting the reduction process.

The Cephalosporin Sulfoxide

The present process can be applied generally to the reduction of any of wide variety of known cephalosporin sulfoxides. Representative of cephalosporin sulfoxides which can be reduced to the corresponding cephalosporin compounds are cephalosporin sulfoxides of the formula

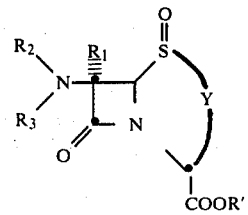

To the extent that there are no unprotected amino or non-enolic hydroxy groups on these starting materials, the nature of the variables $R_1$, $R_2$, $R_3$ and Y are not critical. The groups $R_1$, $R_2$, $R_3$ and Y are typically not affected by the present process. Of course as with most other chemical processes the yields of cephalosporin products from the present process will vary from one cephalosporin to another.

A preferred group of cephalosporin sulfoxide starting materials for the present process are those compounds of the above formula wherein R' is hydrogen or a carboxylic acid protecting group;
$R_1$ is hydrogen or methoxy;

is amino protected by a conventional amino protecting group; or $R_2$ is hydrogen or an acyl group derived from a carboxylic acid, and $R_3$ is an acyl group derived from a carboxylic acid; or $R_2$ and $R_3$ taken together with the nitrogen atom to which they are attached form a group of the formula

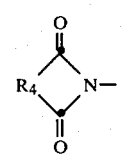

wherein
$R_4$ is the residue of an acyl group derived from a dicarboxylic acid; and Y is a divalent radical selected from the group consisting of

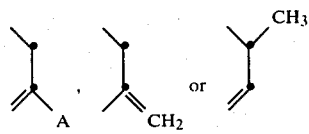

wherein A is hydrogen, chloro, bromo, hydroxy, protected hydroxy, $C_1$–$C_4$ alkoxy, methyl, $C_1$–$C_4$ alkanesulfonyloxy, $C_1$–$C_4$ alkylphenylsulfonyloxy, or a group of the formula —$CH_2B$ wherein B is
(1) $C_2$–$C_4$ alkanoyl, carbamoyloxy, or $C_1$–$C_4$ alkylcarbamoyloxy;

(2) $C_1$–$C_4$ alkoxy;
(3) chloro or bromo;
(4) $C_1$–$C_4$ alkoxycarbonyl or ($C_2$–$C_6$ haloalkoxy)carbonyl; or
(5) a group of the formula —$SR_9$ wherein $R_9$ is
 (a) $C_1$–$C_4$ alkanoyl;
 (b) $C_1$–$C_4$ alkyl, phenyl or phenyl substituted with 1 or 2 substituents selected from the group consisting of $C_1$–$C_4$ alkyl, $C_1$–$C_4$ alkoxy, protected hydroxy, chloro, bromo, fluoro, nitro, cyano, methanesulfonamido and trifluoromethyl; or
 (c) a 5- or 6-membered heterocyclic ring containing 1 to 4 heteroatoms selected from the group consisting of oxygen, sulfur and nitrogen, said ring being unsubstituted or substituted by $C_1$–$C_4$ alkyl, $C_1$–$C_4$ alkoxy, chloro, bromo, oxo, halo ($C_1$–$C_4$ alkyl), protected amino, protected amino ($C_1$–$C_4$ alkyl), protected hydroxy, protected hydroxy ($C_1$–$C_4$ alkyl), protected carboxy, or protected carboxy ($C_1$–$C_4$) alkyl.

Representative of $R_9$ when $R_9$ is an unsubstituted heterocyclicic ring are pyridyl, pyrazinyl, pyridazinyl, pyrimidyl, 1,2,4-triazinyl, pyrazolyl, imidazolyl, thiazolyl, 1,2,4-triazolyl, 1,2,3-triazolyl, 1,2,3-thiadiazolyl, 1,2,4-thiadiazolyl, 1,3,4-thiadiazolyl, 12,3,-oxadiazolyl, 1,2,4-oxadiazolyl, 1,3,4-oxadiazolyl, 1H-tetrazolyl, 2H-tetrazolyl and the like.

A preferred group of heterocyclic rings represented by $R_9$ are

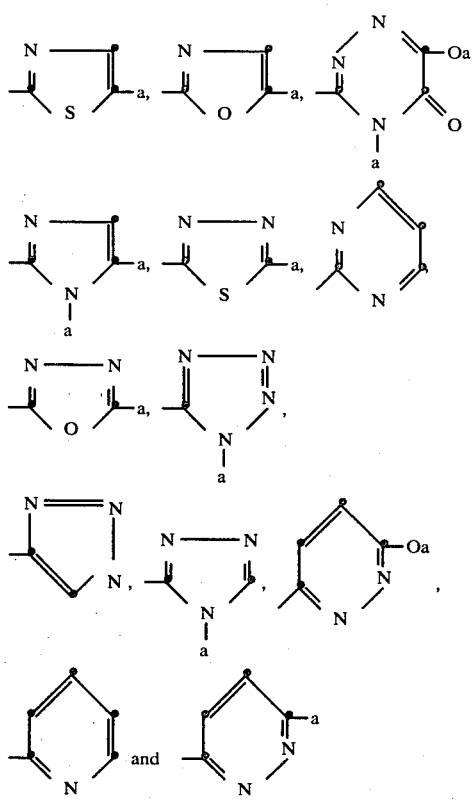

wherein a is hydrogen or $C_1$–$C_4$ alkyl.

The sulfoxides employed in the present process have been described, for example, in the numerous U.S. patents previously cited herein. With reference to the above formula, the compounds wherein A is ($C_1$–$C_4$ alkoxy) carbonyl or ($C_2$–$C_6$ haloalkoxy)-carbonyl are described by Spry in U.S. Pat. No. 3,953,436 issued Apr. 27, 1976. The 3-hydroxy-3-cephem sulfoxides and 3-exomethylenecepham sulfoxides are described by Chauvette in U.S. Pat. No. 3,917,587, issued Nov. 4, 1975 and by Kukolja in U.S. Pat. No. 4,052,387 issued Oct. 4, 1977. Those sulfoxides wherein A is $C_1$–$C_4$ alkanesulfonyloxy or a phenyl or substituted phenylsulfonyloxy group are prepared by the method disclosed in U.S. Pat. No. 3,985,737. The 2-methyl-3-cephems are described in the *Journal of the American Chemical Society*, 97, 5020 (1975) and 98, 2342 (1976). Further, Cooper described a generally applicable method for the synthesis of cephalosporin sulfoxides in U.S. Pat. No. 3,647,786.

When cephalosporin carboxylic acids are employed in the present process yields are typically lower because the kinetic complex reacts not only with the sulfoxide moiety but also with the carboxy group to form the corresponding acid halide which, under normal product isolation procedures, is hydrolyzed to the acid. Preferably, the C-4 carboxy function of the cephalosporin sulfoxide is protected prior to its reduction in the present process. To increase the reduction yields when cephalosporin sulfoxide acids are employed in the present process an additional equivalent of the kinetic complex can be used. A aqueous work-up of the reaction mixture will allow the corresponding cephalosporin acid to be isolated.

In the above description of the cephalosporin sulfoxide reactants for the aforedescribed process embodiment of the present invention, the nitrogen containing C-7 substituent on the cephem sulfoxide substrates can be defined in general terms as (1) and amido group of the formula $R_3NH$- wherein $R_3$ is an acyl group derived from a carboxylic acid; an acylic imido group of the formula $R_2R_3N$- wherein $R_2$ and $R_3$ are acyl groups derived from carboxylic acids or a cyclic imido group of the formula

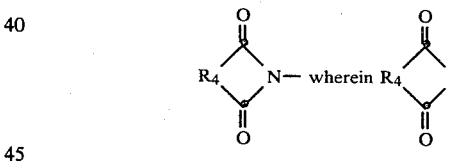

is a diacyl group derived from a dicarboxylic acid. Within this definition of the C-7 substituents the nature of the carboxylic acids from which these groups are derived is not critical to the present processes. The carboxylic acids from which the C-7 substituents are derived are typically $C_1$–$C_{20}$ carboxylic acids. A preferred group of C-7 acylamino substituents for the starting materials for the processes of the present invention is those conventional in the penicillin and cephalosporin art and includes but is not limited to those described in U.S. Pat. Nos. 3,947,413; 3,932,465; 3,954,732; 3,660,396; 3,948,927; 4,052,387; 4,053,469; 4,058,610; 4,066,641 and 4,042,585. Because of the reactivity of the reducing agent utilized in the present invention with protic functional groups, for example carboxy, amino and hydroxy groups, such functional groups if present on the C-7 side chain moiety of the cephem sulfoxide substrate should first be protected using conventional carboxy, amino and hydroxy protecting groups. A non-limiting representation of C-7 acylamino groups for the substrate sulfoxides for the present processes are acylamino groups of the formula $R_7CONH$- wherein $R_7$ is (1) hydrogen, $C_1$–$C_6$ alkyl, halo ($C_1$–$C_4$)-alkyl, cyanomethyl, trifluoromethylthiomethyl, or 4-protected amino-4-protected carboxy butyl;

(2) the group $R_a$ wherein $R_a$ is phenyl or phenyl substituted with 1 or 2 substituents selected from the group consisting of $C_1$–$C_4$ alkyl, $C_1$–$C_4$ alkoxy, protected hydroxy, chloro, bromo, fluoro, iodo, nitro, cyano, carbamyl, methanesulfonamido and trifluoromethyl;

(3) an arylalkyl group of the formula

$R^o$-(Q)$_m$-CQ$_1$Q$_2$- wherein $R^o$ is $R_a$ as defined above, 1,4-cyclohexadienyl, or a 5-membered heterocyclic ring containing 1 to 4 heteroatoms selected from the group consisting of oxygen, nitrogen, and sulfur, said ring being unsubstituted or substituted by $C_1$–$C_4$ alkyl, $C_1$–$C_4$ alkoxy, chloro, bromo, oxo, protected amino, protected amino ($C_1$–$C_4$ alkyl), protected hydroxy or protected carboxy;
m is 1 or 0;
Q is oxygen or sulfur, and
$Q_1$ and $Q_2$ are independently hydrogen or methyl;
subject to the limitation that in the above formula when m is 1, $R^o$ is limited to $R_a$;

(4) a substituted arylalkyl group of the formula

wherein $R^o$ is as defined above and W is ureido, protected amino, protected hydroxy or protected carboxy; or (5) a substituted oximino group of the formula

wherein $R^o$ is defined as in paragraph (3) immediately hereinabove and $R_b$ is $C_1$–$C_4$ alkoxy.

Exemplary of such acylamino groups are formamido, acetamido, propionamido, butyramido, chloroacetamido, 2-bromopropionamido, cyanoacetamido, trifluoromethylthioacetamido, 4-tert-butoxycarbonylamino-4-tert-butoxycarboylbutyramido, benzamido, 4-methylbenzamido, 3-nitrobenzamido, 2-iodobenzamido, 4-benzyloxybenzamido, 3-cyanobenzamido, 2,6-dichlorobenzamido, 4-trifluoromethylbenzamido, 3,4-diethoxybenzamido, and 3-methanesulfonamidobenzamido.

When $R_7$ is a group $R^o$-(Q)$_m$-CQ$_1$Q$_2$- representative acylamino groups are phenylacetamido, 4-bromophenylacetamido, 3,5-dinitrophenylacetamido, 4benzyloxyphenylacetamido, phenoxyacetamido, 4-chlorophenoxyacetamido, 2-propoxyphenoxyacetamido, 4-carbamylphenoxyacetamido, cyclohexadienylacetamido, phenylthioacetamido, 2,5-dichlorophenylthioacetamido, 3-nitrophenylthioacetamido, 2-trifluoromethylphenylthioacetamido, 2-phenylpropionamido, 2-phenoxypropionamido, 2-phenyl-2-methylpropionamido, 2-(4-chlorophenyl)propionamido, 2-furylacetamido, 2-thienylacetamido, 5-isoxazolylacetamido, 2-thiazolylacetamido, 2-thienylpropionamido, 5-thiazolylacetamido, 2-chloroacetamidothiazol-5-ylacetamido, 5-bromothien-2-ylacetamido, 1-tetrazolylacetamido, 5-tetrazolylacetamido and the like.

Illustrative of the acylamino groups when $R_7$ is a substituted arylalkyl group of the formula

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)-acetamido and like groups.

When W is protected carboxy the group $R_7$CONH- can be 2-(4-nitrobenzyloxycarbonyl)-2-(2-thienyl)acetamido, 2-benzhydryloxycarbonyl-2-phenylacetamido, 2-(2,2,2-trichloroethoycarbonyl)-2-(4-chlorophenyl)acetamido, 2-tert-butoxycarbonyl-2-(4-benzyloxyphenyl)acetamido and like groups.

Imido group represented by the formula

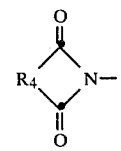

are maleimido, 3-ethylmaleimido, 3,4-dimethylmaleimido, succinimido, phthalimido, and 3,4,5,6-tetrahydrophthalimido.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in *Protective Groups in Organic Chemistry*, J. G. W. McOmie, Ed., Plenum Press, New York, N.Y., 1973, Chapter 2, shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in *Protective Groups in Organic Chemistry*, supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$-$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$-$C_3$ alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and like acid chlorides in the presence of a tertiary amine base. Other known carboxy protecting groups such as those described by E. Halsam in *Protective Groups in Organic Chemistry*, supra, Chapter 5, shall be recognized as suitable. The nature of such ester forming groups is not critical.

In the foregoing definitions hydroxy, amino and carboxy protecting groups are not exhaustively defined. The function of such groups is to protect the reactive function groups during the present process and then be removed at some later point in time without disrupting the remainder of the molecule. Many protecting groups are known in the art, and the use of other protecting groups not specifically referred to hereinabove are equally applicable to the substrates used in the processes of the present invention.

A more preferred group of cephalosporin sulfoxides in the present present process are those of the above formula wherein.

R' is a carboxylic acid protecting group;
$R_1$ is hydrogen;
$R_2$ is hydrogen and $R_3$ is an acyl group of the formula $R_7$CO- wherein $R_7$ is an arylalkyl group of the formula

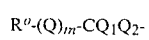

wherein $R^a$ is 2-thienyl, phenyl or substituted phenyl, Q is O, m is 1 or 0, and $Q_1$ and $Q_2$ are hydrogen; and Y is a divalent radical of the formula

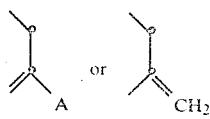

wherein A is as defined above.

The Reaction Conditions

The reduction process of the present invention is conducted in a substantially anhydrous inert organic solvent. Such solvents have been described and exemplified above in the description of the triaryl phosphite-halogen complexes. Preferred solvents for the present process are hydrocarbons, especially aromatic hydrocarbons and halogenated hydrocarbons. Halogenated hydrocarbons other than chloroform are more preferred. Methylene chloride is most preferred.

The present process is usually carried out at a temperature of about 30° C. or below. Preferably the present process is conducted at a temperature of about 10° C. or below. Usually the process is not conducted at a temperature less than about −50° C. Most preferred is a temperature range of about −0° to about −30° C.

It should be noted that the reduction process of the present invention can be conducted at temperatures above 30° C. and below −50° C. The freezing point of the reaction medium, substrate solubility and reaction rates are possible limiting factors at low temperatures while stability of the thermodynamically unstable triaryl phosphite-halogen complex and the product cephalosporins is the main considerations in avoiding selection of higher reaction temperatures. Of course, if the triaryl phosphite-halogen complex has been stabilized in solution with a tertiary amine base as described hereinabove, the upper temperature range for the present process becomes a less critical variable; higher temperatures could easily be employed without significant loss of the reducing agent and without detriment to the reduction process itself.

Typically the present reduction process is carried out simply by adding the cephalosporin sulfoxide either as a solid or in solution to a mixture of the triaryl phosphite-halogen complex (about 1 to about 1.3 molar equivalents per equivalent of sulfoxide) and a halogen scavenger (about 1 to about 3 molar equivalents per equivalent of sulfoxide) in an inert organic solvent at the desired temperature. The course of the reaction can be followed, for example, by comparative thin-layer chromatography. The reduction is usually complete after about 30 minutes to about 2 hours under preferred reaction conditions.. Isolation and purification of the product cephalosporins can be accomplished by conventional laboratory techniques including, for example, extraction, crystallization and recrystallization, filtration, and trituration. The cephalosporin products are known compounds and useful as antibiotics (after removal of protecting groups) or as intermediates to other cephalosporin compounds.

The triaryl phosphite-halogen complexes utilized as reducing agents in the present process are also potent halogenating agents. They can be used to convert both enolic hydroxy groups to the corresponding vinyl chlorides and, in the presence of base, amido groups to the corresponding imino halides. The multiple reactivity of the triaryl phosphite-halogen kinetic complexes is exploited in each of several alternate embodiments of the present invention. Thus, the present invention is also directed to processes for the reduction/halogenation of cephalosporin sulfoxides. These additional aspects of the present invention are illustrated and summarized by reaction schemes I-III:

Scheme I: Reduction/Enol-halogenation

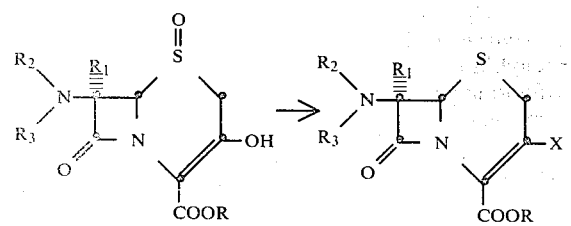

Scheme II: Reduction/Imino-halogenation

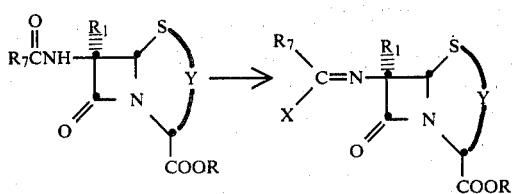

Scheme III:
Reduction/Enol-halogenation/Imino-halogenation

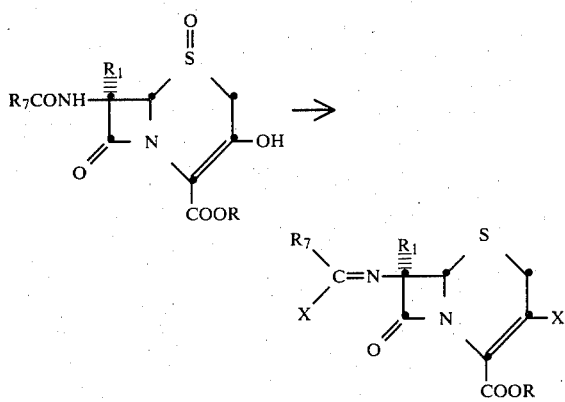

In the above formulas R is a carboxy protecting group and $R_1$, $R_2$, $R_3$, $R_7$, X and Y are as defined hereinabove, provided that when Y is a radical of the formula

A is not hydroxy. The imino halide products of the reactions depicted in Schemes II and III can be isolated or converted by known procedures (alcoholysis via imino ether) to the corresponding nucleus esters

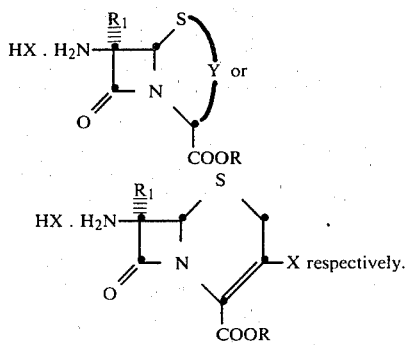

In the reduction/enol-halogenation process of the present invention, illustrated by Scheme I above, a 3-halo cephalosporin is prepared by reacting a 3-hydroxy cephalosporin sulfoxide with about 2 to about 3 equivalents of a triaryl phosphite-halogen kinetic complex of the formula

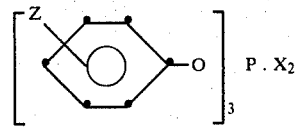

wherein X and Z are as defined hereinabove, in the presence of at least 1 molar equivalent of a scavenger in a substantially anhydrous inert organic solvent at a temperature of about 30° C. or below.

It is preferred that the reduction/enol-halogenation process described above be conducted in the presence of a tertiary amine base. Typically from about 1.0 to about 2.0 equvalents and preferably about 1.5 equivalents of a tertiary amine base is employed for each equivalent of 3-hydroxy cephalosporin sulfoxide used in the reduction/enol-halogenation process. Preferred tertiary amines bases for this process and both the reduction/imino-halogenation (Scheme II) and the reduction/enol-imino-halogenation (Scheme III) described hereinbelow are those having a $pK_b$ value of about 1 to about 10. More preferred are those tertiary amine bases having a $pK_b$ value of about 6 to about 10. Exemplary of suitable teritary amine bases for use in the presence invention are trialkylamines such as trimethylamine, triethylamine, tri-n-propylamine, ethyldimethylamine, benzyldiethylamine and the like; dialkylarylamines such as dimethylaniline, diethylaniline, N,N-diethyl-4-methylaniline, N-methyl-N-ethylaniline, N,N-dimethyltoluidine and the like; cyclic and bicyclic tertiary amines such as pyridine, collidine, quinoline, isoquinoline, 2,6-lutidine, 2,4-lutidine, 1,5-diazabicyclo[4.3.0]-nonene-5 (DBN), 1,5-diazabicyclo[5.4.0]undecene-5 (DBU), triethylenediamine and the like; and polymeric tertiary amine bases such as the copolymer formed from divinylbenzene and vinylpyridine described by Hallensleben and Wurm in *Angew. Chem. Intl. Ed. Engl.*, 15, 163 (1976). Pyridine is a preferred tertiary amine base.

With reference to Scheme II above, representing another embodiment of the present invention, cephalosporin imino halides are prepared by reacting 7-acylamino cephalosporin sulfoxides with about 2 to about 3 equivalents of one of the triaryl phosphite halogen kinetic complexes of the formula

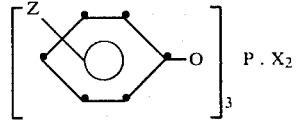

detailed hereinabove, in the presence of at least 1 equivalent of a halogen scavenger and about 1.0 to about 2.0 equivalents of a tertiary amine base in a substantially anhydrous organic solvent at a temperature of about 30° C. or below.

Scheme III above represents a preferred embodiment of the present invention wherein a 3-halocephalosporin imino halide is prepared by reacting a 7-acylamino-3-hydroxy cephalosporin with about 3 to about 5 equivalents of one of the triaryl phosphite-halogen complexes of the formula

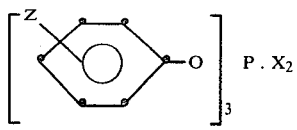

described hereinabove in the presence of at least 1 equivalent of a halogen scavenger and about 2 to about 5 equivalents of a tertiary amine base in a substantially anhydrous inert organic solvent at a temperature of about 30° C. or below. Best results for the Scheme III process where X=Cl have been observed when about 4.4 equivalents of triphenyl phosphitechlorine kinetic complex and about 3.8 equivalents of pyridine are employed to each equivalent of 7-acylamino-3-hydroxycephalosporin sulfoxide starting material using methylene chloride as a solvent.

The multi-effect/single step process embodiments of the present invention illustrated in Schemes I-III above are conducted under essentially the same conditions detailed hereinabove for the general reduction of cephalosporin sulfoxides using triaryl phosphite-halogen complexes. Except for the particular structural requirements for the cephalosporin sulfoxide reactants, the requirement for the presence of a tertiary amine base in the processes of Schemes II and III, and the stoichiometry unique to the individual multi-conversion processes, all reaction parameters for the multi-conversion processes of Schemes I-III are identical to those described for the basic sulfoxide reduction process of this invention. This includes the aforedescribed temperature ranges, solvents, triaryl phosphite-halogen kinetic complexes, halogen scavengers and preferences therefor.

Thus, in general, the processes illustrated by Schemes I-III are conducted at temperatures between about −50° and about 30° C. with reaction temperatures of about −50° to about 10° C. being preferred and about −30° to about 0° C. being most preferred when X is Cl. Lower temperatures (about −50° to about −20° C.) are typically used when the kinetic complex is derived from a triaryl phosphite and bromine. Both aromatic hydrocarbon and halogenated hydrocarbon solvents are preferred, however the process depicted by Scheme III has been found to proceed without disadvantage in acetonitrile and tetrahydrofuran. Although halogenated hydrocarbon solvents are in general most preferred for the present processes it should be noted that chloroform has been found to be the least satisfactory halogenated hydrocarbon solvent. Kinetic complexes derived from triaryl phosphites and chlorine (X=Cl) are preferred; the triphenyl phosphite-chlorine kinetic complex (X=Cl, Z=H) is most preferred. Preferred halogen scavengers are $C_2$-$C_6$ alkenes. Typically about 1 to about 3 molar equivalents of halogen scavenger is used for each equivalent of starting material.

The tertiary amine base used in the present reduction/imino-halogenation and the present reduction/imino-enol-halogenation processes (and preferably in the present reduction/enol-halogenation process) is typically added to the reaction mixture after the substrate cephalosporin sulfoxide has been added to, and allowed to react with, a mixture of the triaryl phosphite-halogen complex and halogen scavenger in the solvent medium. However, the reaction need not be carried out in this manner. The addition of the tertiary amine, for example, can be initiated with the addition of the sulfoxide reactant, or a portion of it can be added to the solution of the kinetic complex to be used in the process, stabilizing that reagent until the cephalosporin sulfoxide is added to the reaction mixture.

The cephalosporin products of the present processes can be isolated and purified by conventional laboratory techniques including, for example, extraction, crystallization and recrystallization, and trituration. Because the imino halide products are sensitive to acid catalyzed alcoholysis or hydrolysis and to nucleophilic attack, some precaution should be taken during product isolation to avoid exposing the products to conditions under which such reactions of the imino halide might take place. For example, under neutral conditions achieved by maintaining a concentration of a non-nucleophilic acid scavenger such as propylene oxide, solutions of the imino halide products can be washed with water and brine and evaporated, usually under reduced pressure, to provide the product in substantially pure form.

Since the primary utility of the imino halide products is as intermediates to the corresponding C-7 aminocephalosporins, preferably the imino halide products of the present process are reacted without isolation from the reducing/halogenating reaction mixture with an excess of a $C_1$-$C_{15}$ aliphatic alcohol or more preferably a β-disubstituted primary aliphatic alcohol or a 1,2- or 1,3-diol to provide the corresponding nucleus esters.

The improved alcoholysis of cephem imino halides via an imino ether intermediate using β-disubstituted aliphatic alcohols and 1,2- or 1,3-diols to provide cephem nucleus esters is disclosed in U.S. Pat. Nos. 3,845,043, issued Oct. 29, 1974, and 3,868,368 issued Feb. 25, 1975 respectively.

Preferred for imino etherification and subsequent alcoholysis of the imino halide products are a $C_4$-$C_{12}$ β-disubstituted primary aliphatic alcohol, a $C_3$-$C_{15}$ aliphatic 1,3-diol, or a $C_2$-$C_{12}$ aliphatic 1,2-diol.

Suitable β-disubstituted primary aliphatic alcohols are those compounds of the formula

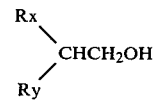

wherein each of Rx and Ry is an alkyl group such that the β-disubstituted primary aliphatic alcohol has from 4 to about 12 carbon atoms or Rx and Ry are taken together with the carbon atom to which they are bonded to form a cycloalkyl group having from 5 to 8 carbon atoms. Exemplary of such alcohols are isobutanol, 2-methylbutanol, 2-ethylbutanol, 2-ethylhexanol, hydroxymethylcyclopentane, hydroxymethylcyclohexane, 2-n-butyloctanol, 2-n-propyl-hexanol and like alcohols. Suitable 1,2 or 1,3-diols are those of the formula

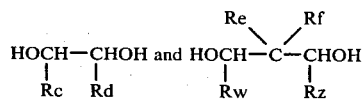

respectively wherein Rc and Rd are hydrogen or alkyl such that the 1,2-diol has from 2 to 12 carbon atoms and wherein Rw and Rz are each hydrogen, methyl or ethyl, and each of Re and Rf is hydrogen or a hydrocarbon moiety such that the 1,3-diol has from 3 to 15 carbon atoms. Representative of 1,2-diols are 1,2-propylene glycol, 2,3-butanediol, 1,2-butanediol, 3,4-pentanediol, and 3,4-hexanediol. Representative of 1,3-diols are 1,3-propanediol, 1,3-butanediol, 1,3-pentanediol, 2,2-dimethyl-1,3-propanediol, 2,2-diethyl-1,3-propanediol, 2,4-pentanediol, and 2,2-diphenyl-1,3-propanediol. Most preferred of alcohols or diols for cleavage of the imino-halide products of the present process are isobutanol, 1,2-propanediol and 1,3-propanediol.

An excess of the alcohol or diol is employed for cleavage of the imino halide products of the process of the present invention. The amount of excess alcohol or diol is not critical. When the aforedescribed 1,2- or 1,3-diols are employed about a 2-3 fold excess will suffice. When a β-disubstituted primary aliphatic alcohol is employed about a 3-6 fold excess is usually preferred. Of course larger amounts of the alcohol or diol may be employed without affecting the course of the reaction. Often a 10-15 fold excess of the preferred alcohol or diol is used. In general a 3 to 15 fold excess of alcohol or diol is preferred. When aliphatic alcohols other than those mentioned hereinabove as preferred are used to cleave the imino halide products of the present process, larger excesses, about 10-100 fold, are typically employed.

Usually the alcohol or diol is simply added to the halogenating reaction mixture in which the imino chloride has been prepared in accordance with the process of the present invention.

Alcoholysis of the imino halide (via imino ether formation) is acid catalyzed. The reaction mixture itself is usually acidic enough so that alcoholysis occurs upon alcohol or diol addition without the addition of acid to the reaction mixture. However, to enhance the rate of alcoholysis and therefore the rate of nucleus ester formation, the reaction mixture is preferably acidified with, for example, hydrogen chloride after the alcohol or diol has been added to the reaction mixture. This can be accomplished simply by bubbling HCl gas into the reaction mixture for a short period of time. Other acids, organic and inorganic can, however, be employed. Typically at least about 1 equivalent of hydrogen chloride is added to the reaction mixture to promote nucleus ester formation.

The product nucleus esters can be isolated often as their crystalline hydrochloride salts simply by filtering the crystallized product from the reaction mixture. Non-crystalline nucleus esters produced in accordance with the present procedure can be isolated from the reaction mixture using conventional laboratory techniques. Alternatively, the nucleus esters can be reacted (acylated) in solution, without being isolated. Acylation of the nucleus esters using well known laboratory procedures provides C-7 acylamino cephalosporins esters which either can be deesterified to provide known antibiotic compounds or they can be used as intermediates for further chemical modification.

Combining the aforedescribed reduction/enol-imino halogenation (Scheme III above), using a triaryl phosphite-chlorine complex, with subsequent alcoholysis of the resulting imino chloride constitutes an improved method of preparation of 7-amino-3-chloro-3-cephem-4-carboxylic acid esters from the corresponding 7-acylamino-3-hydroxy-3-cephem-4-carboxylic acid ester sulfoxides. Prior to this invention the total 3-function conversion was effected either in 3 separate steps, that is reduction, chlorination and side chain cleavage or in two steps, either combining reduction and chlorination (see U.S. Pat. No. 4,115,643) with subsequent side chain cleavage or by combining chlorination and side chain cleavage after reduction of the sulfoxide entity, for example, using the method disclosed in U.S. Pat. No. 4,044,002. With the discovery of the present process the reduction, chlorination and cleavage conversions can be effected in excellent yields in one reaction vessel without isolation of intermediates.

The 3-halocephem nucleus esters are known compounds. They can be acylated using conventional acylation techniques and subsequently deesterified to provide known antibioitic compounds. Of particular significance is the utility of these nucleus ester intermediates in the preparation of 7-(D-2-phenyl-2-aminoacetamido-3-chloro-3-cephem-4-carboxylic acid, a relatively new and clinically significant antibiotic.

In a preferred process embodiment of the present invention a 7-amino-3-chloro-3-cephem-4-carboxylic acid ester hydrochloride of the formula

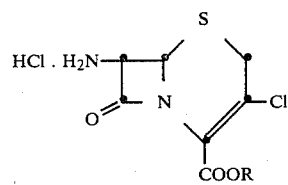

is prepared by
(a) reacting a 7-acylamino-3-hydroxy-3-cephem-4-carboxylic acid ester sulfoxide with about 4.0 to about 5.0 equivalents of the kinetically controlled product of the reaction of equivalent amounts of triphenyl phosphite and chlorine in a substantially anhydrous inert organic solvent, in the presence of about 3.5 to about 4.0 equivalents of pyridine and about 1 to about 3 equivalents of a $C_2$-$C_6$ alkene in a substantially anhydrous inert organic solvent, at a temperature of about $-10°$ to about $-30°$ C.;
(b) adding about 3 to about 15 equivalents of isobutanol, 1,3-propanediol or 1,2-propanediol to the reaction mixture after formation of the 3-chloro-3-cephem imino chloride is complete; and
(c) acidifying the reaction mixture with HCl.

A most preferred inert organic solvent is methylene chloride.

Preferred 3-hydroxy-3-cephem sulfoxide substrates are those bearing conventional penicillin and cephalosporin carboxamido groups at the C-7 position. A particularly preferred group of 3-hydroxy-3-cephem sulfoxides are those bearing an acylamino group of the formula $R^o$-$(Q)_m$-$CQ_1Q_2CONH$-wherein $R^o$ is 2-thienyl, phenyl or substituted phenyl, Q is O, m is 1 or 0 and $Q_1$ and $Q_2$ are hydrogen. More preferred for economic reasons and not necessarily for reactivity are the $C_7$-substituents phenylacetamido, phenoxyacetamido and 2-thienylacetamido. Similarly the 4-nitrobenzyl group is a preferred carboxy protecting group in the preferred process embodiment because of the crystalline nature of the product hydrochloride, and therefore the ease of isolation of a product nucleus ester of high purity.

The following examples are provided to further illustrate the present invention. It is not intended that this invention be limited in scope by reason of any of these examples. In the following examples and preparations nuclear magnetic resonance spectra are abbreviated nmr. The chemical shifts are expressed in δ values in parts per million (ppm) and coupling constants (J) are expressed in Hz (cycles per second).

EXAMPLE 1

4'-Nitrobenzyl 7-phenylacetamido-3-methylenecepham-4-carboxylate

To 75 ml. of methylene chloride at −20° C., chlorine gas and 10 ml. of triphenyl phosphite were added at such a rate that a pale green color persisted in the reaction medium throughout the co-addition. The temperature of the reaction medium was maintained at −20° to −25° C. After the addition was complete, 3 ml. of amylene was added. The resulting solution of triphenyl phosphite-chlorine kinetic complex (TPP-C) was stored at −30° C.

To a stirred mixture of 5.0 ml. of the above described TPP-C solution and 0.5 ml of amylene was added 500 mg. of 4'-nitrobenzyl 7-phenylacetamido-3-methylenecepham-4-carboxylate 1-oxide. After the reaction mixture was stirred at 10° C. for 45 minutes, 2 ml. of methanol was added. The mixture was evaporated in vacuo to dryness. The product residue was slurried with ether. Filtration afforded 410 mg. of the title product.

Nuclear magnetic resonance data for this product and those products from Examples 2–8 are presented in tabular form in Table II hereinbelow.

EXAMPLE 2

4'-Nitrobenzyl 7-phenoxyacetamido-3-methylenecepham-4-carboxylate

In accordance with the procedure described in Example 1 500 mg. of 4'-nitrobenzyl 7-phenoxyacetamido-3-methylenecepham-4-carboxylate, 1-oxide was reduced to provide 370 mg. of the title product.

EXAMPLE 3

4'-Nitrobenzyl 7-phenoxyacetamido-3-chloro-3-cephem-4-carboxylate

In accordance with the procedure described in Example 1, 500 mg. of 4'-nitrobenzyl 7-phenoxyacetamido-3-chloro-3-cephem-4-carboxylate, 1-oxide was reduced to provide 310 mg. of the title product.

EXAMPLE 4

4'-Nitrobenzyl 7-(2-thienylacetamido)-3-methyl-3-cephem-4-carboxylate

Following the experimental procedure described in Example 1, 500 mg. of 4'-nitrobenzyl 7-(2-thienylacetamido)-3-cephem-4-carboxylate, 1-oxide was reduced to provide 260 mg. of the title product.

EXAMPLE 5

4'-Nitrobenzyl 7-heptanolyamino-3-methyl-3-cephem-4-carboxylate

In accordance with the procedure described in Example 1, 500 mg. of 4'-nitrobenzyl 7-heptanoylamino-3-methyl-3-cephem-4-carboxylate, 1-oxide was reduced to provide 270 mg. of the title product.

EXAMPLE 6

4'-Methoxybenzyl 7-(2-thienylacetamido)-3-methyl-3-cephem-4-carboxylate

Following the procedure described in Example 1, 500 mg. of 4'-methoxybenzyl 7-(2-thienylacetamido)-3-cephem-4-carboxylate, 1-oxide was reduced to provide 470 mg. of the title product.

EXAMPLE 7

Benzyl 7-(2-thienylacetamido)-3-methyl-3-cephem-4-carboxylate

Following the same general procedure in Example 1, 300 mg. of benzyl 7-(2-thienylacetamido)-3-methyl-3-cephem-4-carboxylate, 1-oxide was reduced using 3 ml. of the described solution of triphenyl phosphite-chlorine complex and 0.3 ml. of amylene to provide 240 mg. of the title product.

EXAMPLE 8

2',2',2'-Trichloroethyl 7-phenoxyacetamido-3-methylenecepham-4-carboxylate

Following the same general procedure described in Example 1, 300 mg. of 2',2',2'-trichloroethyl-7-phenoxyacetamido-3-methylenecepham-4-carboxylate, 1-oxide was reduced using 3 ml. of the TPP-C solution and 0.3 ml. of amylene to provide 80 mg. of the title product.

Table II

| Example No. | Nuclear magnetic resonance data (CDCl$_3$) δ for products of Examples 1–8. | | | | | |
|---|---|---|---|---|---|---|
| | C-2H | C-6H | C-7H | NH | ester-CH$_2$ | side chain CH$_2$ |
| 1 | 3.60 | 5.27 | 5.50 | 9.13 | 5.45 | 3.60 |
| 2 | 3.53 | ~5.3 | ~5.5 | 9.07 | ~5.4 | 4.63 |
| 3 | 3.93 | !5.30 | 5.83 | 9.18 | 5.26 | 3.78 |
| 4 | 3.60 | 5.15 | 5.73 | 9.05 | 5.45 | 3.83 |
| 5 | 3.55 | 5.12 | 5.68 | 8.67 | 5.45 | |
| 6 | 3.50 | 5.07 | 5.63 | 9.05 | 5.18 | 3.78 |
| 7 | 3.50 | 5.07 | 5.63 | 9.13 | 5.26 | 3.78 |
| 8 | 3.63 | ~5.3 | ~5.5 | 9.13 | 5.02 | 4.63 |

EXAMPLE 9

4'-Nitrobenzyl 7-phenoxyacetamido-3-methylenecepham-4-carboxylate using stabilized TTP-C To a solution of 0.8 ml (10 mmol) of pyridine in 150 ml. of methylene chloride at −20° C., chlorine gas and 20 ml. of triphenyl phosphite were added at such a rate that a pale green color persisted throughout the co-addition. The temperature of the reaction medium was held at −20° C. To the resulting solution of stabilized triphenyl phosphite-chlorine kinetic complex were added 8 ml. of amylene and 19.13 gm. of 4'-nitrobenzyl 7-phenoxyacetamido-3-methylenecepham-4-carboxylate, 1-oxide. The reaction mixture was stirred for about 1 hour at −15° to −20° C. The mixture was then warmed to room temperature and concentrated in vacuo to a syrup. Methanol (40 ml.) was added. After stirring for 30 minutes the solution was filtered affording 11.58 gm. of the title product-confirmed by nmr comparision with authentic material.

EXAMPLE 10

4'-Nitrobenzyl 7-phenoxyacetamido-3-hydroxy-3-cephem-4-carboxylate

A solution of TTP-C complex was prepared by the co-addition of 6.1 ml. of triphenyl phosphite and chlorine to 45 ml. of methylene chloride at −15° C. Triphenyl phosphite was added until starch-iodide test was negative for chlorine. To the resulting solution at −15° C. were added 3 ml. of amylene and 10.6 gm. of 4'-nitrobenzyl 7-phenoxyacetamido-3-hydroxy-3-cephem-4-carboxylate, 1-oxide. After 40 minutes the reaction mixture was allowed to warm to room temperature and then filtered to remove unreacted starting material (5.08 gm.). The filtrate was concentrated in vacuo to about 35 ml. After cooling the solution to 0° C. acetic acid (10 ml.) was added. Filtration provided, in two crops, 1.81 grams of the acetic acid solvate of the title product.

nmr (CDCl$_3$) δ 2.05 (s, 3, C$\underline{H}_3$COOH), 3.67 (bs, 2), 4.53 (s, 2), 5.01 (d, 1, J=4 Hz), 5.31 (ABq, 2), 5.65 (q, 1, J=4 and 9 Hz) and 6.8–8.4 (ArH).

EXAMPLE 11

4'-Nitrobenzyl 7-phenoxyacetamido-3-chloro-3-cephem-4-carboxylate

Following the same procedure described in Example 10, 17.1 ml. of triphenyl phosphite was used to prepare the TPP-C complex in 70 ml. of methylene chloride at −20° C. Amylene (2.2 ml.) was added followed by 10.6 gm. of 4-nitrobenzyl 7-phenoxyacetamido-3-hydroxy-3-cephem-4-carboxylate, 1-oxide. The temperature of the reaction mixture rose to −8° C. After 45 minutes, the addition of a solution of 3 ml. of pyridine in 15 ml. of methylene chloride over a 70 minute period was begun. The reaction temperature was maintained at −10° to −15° C. for 45 minutes after the addition of pyridine was complete. The reaction mixture was concentrated in vacuo to about 35 ml., and 10 ml. of ethanol (2B) was added. Further concentration of the solution and the addition of several ml. of acetic acid resulted in crystallization of 3.2 g. (in two crops) of the title product which was isolated by filtration. Structure of the product was confirmed by nmr comparison with authentic sample of title product.

EXAMPLE 12

4'-Nitrobenzyl 7-amino-3-chloro-3-cephem-4-carboxylate, hydrochloride

A solution of triphenyl phosphite-chloride kinetic complex was prepared by adding chlorine and triphenyl phosphite (36.8 ml., 3.5 equivalents per equivalent of cephem sulfoxide used below −22.3 g.) simultaneously to 150 ml. of methylene chloride at about −20° to about −10° C., maintaining a pale yellow color in the reaction mixture throughout the co-addition. With the addition of the last drops of triphenyl phosphite to the mixture, it gave a negative starch-iodide test for chlorine. After cooling the mixture to −25° C., 5.1 ml. of amylene and subsequently 22.3 gm. of 4'-nitrobenzyl 7-phenoxyacetamido-3-hydroxy-3-cephem-4-carboxylate, 1-oxide were added. After stirring 25 minutes at −15° to −10° C., the dropwise addition of 11 ml. (3.4 equivalents per equivalent of cephem sulfoxide) of pyridine in 30 ml. of methylene chloride was begun. Pyridine addition was extended over 53 minutes. Fifteen minutes after pyridine addition was complete, 37 ml. (10 equivalents) of isobutanol was added and HCl was bubbled into the reaction mixture for 6 minutes. The title product crystallized from solution and was isolated by filtration, washed with 100 ml. of methylene chloride and dried in vacuo. Yield—6.4 g. (37%).

nmr (DMSO-d$_6$) δ 4.06 (bs, 2), 5.33 (q, 2, J=4.5 Hz, β-lactam H), 5.5 (s, 2), 7.8-83 (ArH) and ∼8.6 (very broad s, −NH$_3$+).

EXAMPLES 13–56

The reaction described in Example 12 was studied in detail in an attempt to optimize reaction conditions. Table III summarizes the results of these studies. The same general procedure was followed as described in Example 12 using the amounts of reagents and reaction times indicated in the Table. The substrate cephem sulfoxide and its amount (22.3 g.), the amount of methylene chloride solvent for the pyridine (30 ml.), and the amount of isobutanol (37 ml.) was held constant in each of the tabulated examples.

Table III

Summary of Results for Examples 12–56

| Ex. No. | TPP-C (equiv*) | TPP (mls) | ta** (min) | Amylene (ml/equiv*) | CH$_2$Cl$_2$ (ml) | tb*** (min) | Pyridine (ml/equiv) | Product (gm, % corrected yield) |
|---|---|---|---|---|---|---|---|---|
| 12 | 3.5 | 36.8 | 25 | 5.1/1.2 | 150 | 53 | 11.0/3.4 | 6.4/37.0 |
| 13 | 4.5 | 47.3 | 55 | 5.1/1.2 | 150 | 99 | 13.6/4.2 | 12.42/71.6 |
| 14 | 4.0 | 42.1 | 40 | 5.1/1.2 | 150 | 76 | 12.3/3.8 | 13.06/76.4 |
| 15 | 4.5 | 47.3 | 25 | 5.1/1.2 | 150 | 53 | 13.6/4.2 | 12.94/75.7 |
| 16 | 3.5 | 36.8 | 55 | 5.1/1.2 | 150 | 99 | 13.6/4.2 | 9.48/55.9 |
| 17 | 4.5 | 47.3 | 55 | 5.1/1.2 | 150 | 99 | 11.0/3.4 | 12.13/70.6 |
| 18 | 3.5 | 36.8 | 55 | 5.1/1.2 | 150 | 53 | 13.6/4.2 | 7.73/44.8 |
| 19 | 4.0 | 42.1 | 40 | 5.1/1.2 | 150 | 122 | 12.3/3.8 | 13.32/78.3 |
| 20 | 3.5 | 36.8 | 25 | 5.1/1.2 | 150 | 53 | 13.6/4.2 | 9.52/55.1 |
| 21 | 4.0 | 42.1 | 40 | 5.1/1.2 | 150 | 76 | 9.7/3.0 | 5.43/31.7 |
| 22 | 4.0 | 42.1 | 10 | 5.1/1.2 | 150 | 76 | 12.3/3.8 | 13.58/79.2 |
| 23 | 4.5 | 47.3 | 55 | 5.1/1.2 | 150 | 53 | 11.0/3.4 | 11.65/68.6 |
| 24 | 3.5 | 36.8 | 55 | 5.1/1.2 | 150 | 53 | 11.0/3.4 | 10.37/61.2 |
| 25 | 4.0 | 42.1 | 40 | 5.1/1.2 | 150 | 76 | 12.3/3.8 | 12.24/70.8 |
| 26 | 4.5 | 47.3 | 25 | 5.1/1.2 | 150 | 99 | 13.6/4.2 | 12.35/73.3 |
| 27 | 4.0 | 42.1 | 40 | 5.1/1.2 | 150 | 76 | 12.3/3.8 | 12.85/75.5 |
| 28 | 4.0 | 42.1 | 40 | 5.1/1.2 | 150 | 76 | 14.9/4.6 | 12.36/71.4 |
| 29 | 3.0 | 31.6 | 40 | 5.1/1.2 | 150 | 76 | 12.2/3.8 | —/∼5 |
| 30 | 3.5 | 36.8 | 55 | 5.1/1.2 | 150 | 99 | 11.0/3.4 | 9.15/54.2 |
| 31 | 3.5 | 36.8 | 25 | 5.1/1.2 | 150 | 99 | 13.6/4.2 | 7.69/44.7 |

Table III-continued

Summary of Results for Examples 12-56

| Ex. No. | TPP-C (equiv*) | TPP (mls) | ta** (min) | Amylene (ml/equiv*) | $CH_2Cl_2$ (ml) | tb*** (min) | Pyridine (ml/equiv) | Product (gm, % corrected yield |
|---|---|---|---|---|---|---|---|---|
| 32 | 4.0 | 42.1 | 40 | 5.1/1.2 | 150 | 76 | 12.3/3.8 | 12.18/72.1 |
| 33 | 5.0 | 52.7 | 40 | 5.1/1.2 | 150 | 76 | 12.3/3.8 | 13.48/78.8 |
| 34 | 4.0 | 42.1 | 70 | 5.1/1.2 | 150 | 76 | 12.3/3.8 | 12.93/75.6 |
| 35 | 4.5 | 47.3 | 55 | 5.1/1.2 | 150 | 53 | 13.6/4.2 | 13.25/77.2 |
| 36 | 4.5 | 47.3 | 25 | 5.1/1.2 | 150 | 53 | 11.0/3.4 | 12.66/73.6 |
| 37 | 4.5 | 47.3 | 25 | 5.1/1.2 | 150 | 99 | 11.0/3.4 | 11.45/66.3 |
| 38 | 3.5 | 36.8 | 25 | 5.1/1.2 | 150 | 99 | 11.0/3.4 | 10.70/61.8 |
| 39 | 4.0 | 42.1 | 40 | 5.1/1.2 | 150 | 30 | 12.3/3.8 | 12.42/72.2 |
| 40 | 4.0 | 42.1 | 0 | 5.1/1.2 | 150 | 76 | 12.3/3.8 | 13.16/76.5 |
| 41 | 4.0 | 42.1 | 40 | 0 | 150 | 76 | 12.2/3.8 | 0/0 |
| 42 | 4.0 | 42.1 | 10 | 5.1/1.2 | 150 | 76 | 9.0/2.8 | 3.32/18.3 |
| 43 | 4.0 | 42.1 | 40 | 5.1/1.2 | 100 | 76 | 12.3/3.8 | 12.68/72.3 |
| 44 | 4.0 | 42.1 | 10 | 5.1/1.2 | 150 | 76 | 12.3/3.8 | 8.2/48.4 |
| 45 | 4.0 | 42.1 | 10 | 6.4/1.5 | 150 | 76 | 12.3/3.8 | 13.33/78.6 |
| 46 | 4.0 | 42.1 | 10 | 6.4/1.5 | 150 | 76 | 12.3/3.8 | 13.90/81.0 |
| 47 | 4.0 | 42.1 | 10 | 8.5/2.0 | 200 | 76 | 12.3/3.8 | 13.19/75.4 |
| 48 | 4.0 | 42.1 | 10 | 5.1/1.2 | 150 | 76 | 12.3/3.8 | 14.4/83.1 |
| 49 | 4.0 | 42.1 | 10 | 6.4/1.5 | 150 | 40 | 12.3/3.8 | 13.16/75.7 |
| 50 | 4.2 | 44.5 | 10 | 6.4/1.5 | 150 | 76 | 12.3/3.8 | 13.54/81.6 |
| 51 | 4.2 | 44.5 | 10 | 6.4/1.5 | 200 | 40 | 12.3/3.8 | 11.05/65.0 |
| 52 | 4.2 | 44.5 | 10 | 6.4/1.5 | 200 | 60 | 12.3/3.8 | 14.09/82.8 |
| 53 | 4.2 | 44.5 | 10 | 6.4/1.5 | 200 | 60 | 12.3/3.8 | 14.00/81.7 |
| 54 | 4.4 | 46.3 | 10 | 6.4/1.5 | 200 | 60 | 12.3/3.8 | 14.16 |
| 55 | 4.4 | 46.3 | 10 | 6.4/1.5 | 200 | 60 | 12.3/3.8 | 14.35 |
| 56 | 4.2 | 44.5 | 10 | 6.4/1.5 | 200 | 60 | 12.3/3.8 | 13.77 |

*equivalents per each equivalent of cephem sulfoxide starting material
**ta is the time after cephem sulfoxide addition that pyridine addition started
***tb is the time period over which the pyridine solution is added to the reaction mixture

EXAMPLE 57

4'-Nitrobenzyl 7-amino-3-chloro-3-cephem-4-carboxylate

A solution of the triphenyl phosphitechlorine (TPP-C) complex was prepared from 23 ml. of triphenyl phosphite and chlorine in 100 ml. of methylene chloride by the procedure described in Example 12. To this solution at −10° to −15° C. was added 5.28 ml. of cyclopentene (3.0 equivalents per equivalent of cephem sulfoxide starting material) and subsequently 11.15 gm. of 4'-nitrobenzyl 7-phenoxyacetamido-3-hydroxy-3-cephem-4-carboxylate, 1-oxide. A solution of 6.2 ml. of pyridine in 15 ml. of methylene chloride was added dropwise over a 60 minute period while the reaction temperature was maintained at −10° to −15° C. Thereafter 18.5 ml. of isobutanol was added and gaseous HCl was bubbled through the mixture for about 3 minutes. The reaction mixture was then allowed to warm to room temperature, and after 2 hours was filtered to provide the title product in 80.4% yield.

EXAMPLES 58-61

The same procedure and reagent amounts (equiv.) were used as described in Example 57, except that the halogen scavenger was varied. Table IV summarizes the results of Example 57-61.

Table IV

Summary of Examples 57-61

| Ex. No. | Scavenger | amount (3.0 equiv.) | Yield(%) |
|---|---|---|---|
| 57 | cyclopentene | 5.28 ml. | 80.4 |
| 58 | cyclohexene | 6.08 ml. | 72.8 |
| 59 | cycloheptene | 7.1 ml. | 78.2 |
| 60 | 1,5-cyclooctadiene | 7.4 ml. | 73.4 |
| 61 | m-dimethoxybenzene | 7.9 ml. | 60.5 |

EXAMPLE 62

4'-Nitrobenzyl 7-amino-3-chloro-3-cephem-4-carboxylate, hydrochloride (acetonitrile)

(A) Following the general procedure described in Example 12 the TPP-C complex was prepared from chlorine and 23.0 ml. of triphenyl phosphite in 100 ml. of acetonitrile. To that solution were added 3.2 ml. of amylene and 11.15 gm. of 4'-nitrobenzyl 7-phenoxyacetamido-3-hydroxy-3-cephem-4-carboxylate, 1-oxide. Pyridine (6.2 ml.) in acetonitrile was then added dropwise. After the pyridine addition was complete 18.5 ml. of isobutanol was added. Gaseous HCl was bubbled into the reaction mixture during which time the temperature of the reaction mixture rose to 40° C. An ice bath was used to cool the mixture to about 25° C. The title product crystallized from the mixture at 28° C. and was isolated in 46.5% yield.

(B) The same general procedure was followed as described in Paragraph A above except that 100 ml. of tetrahydrofuran was used as the reaction medium. About 25 ml. of methylene chloride was added to the mixture after the addition of the isobutanol and HCl. Yield of title product - 35.1%.

EXAMPLE 63

4'-Nitrobenzyl 7-amino-3-chloro-3-cephem-4-carboxylate hydrochloride (room temperature)

A solution of triphenyl phosphite-chlorine complex was prepared by adding chlorine and 22.9 ml. of triphenyl phosphite simultaneously to a mixture of 0.93 ml. of pyridine in 100 ml. of methylene chloride at 21° to 25° C. The reagents were added to such a rate that a pale green color persisted in the reaction mixture throughout the co-addition. To this solution were added 4.2 ml. of amylene and subsequently 11.2 grams of 4-nitrobenzyl 7-phenoxyacetamido-3-chloro-3-cephem-4-carboxylate, 1-oxide. The reaction temperature rose to about 30° C. It was cooled to 22° before 5.3 ml. of pyridine in 15 ml. of methylene chloride was added dropwise over a period of 1 hour. Fifteen minutes after pyridine addition was completed 18.5 ml. of isobutanol was added. HCl was bubbled into the solution for 5 minutes. Filtration after 2 hours afforded 5.69 grams of the title product.

EXAMPLE 64

4'-Nitrobenzyl 7-amino-3-methylenecepham-4-carboxylate, hydrochloride

Triphenyl phosphite-chlorine complex was prepared from chlorine and 31.6 ml. of triphenyl phosphite by the procedure described in Example 12. Amylene (5.1 ml.) and 4'-nitrobenzyl 7-phenoxyacetamido-3-methylenecephem-4-carboxylate 1-oxide (19.13 gm.) were added. After 30 minutes the dropwise addition of 6.3 ml. of pyridine in 16 ml. of methylene chloride was initiated. The addition was extended over 1 hour. After 15 minutes and additional 3.1 ml. of pyridine in 8 ml. of methylene chloride was added over ½ hour. Fifteen minutes after the final addition of pyridine was complete 37 ml. of isobutanol was added. HCl was bubbled through the reaction mixture for 6 minutes. Filtration after 2 hours provided 10.5 gm. (69.5%) of the title product.

nmr (DMSO-d$_6$) δ 3.67 (bs, 2), 5.0 (d, 1, J=5 Hz), 5.35-5.53 (m, 6) and 7.6-8.4 (m, ArH).

EXAMPLE 65

4'-Nitrobenzyl 7-phenoxyacetamido-3-methylenecepham-4-carboxylate. Triphenyl phosphite-bromine kinetic complex (A) A solution of triphenyl phosphitebromine complex was prepared by adding 19.9 ml. of triphenyl phosphite to 3.9 ml. of bromine in 150 ml. of methylene chloride at −30° C. A faint color was noted in the reaction mixture even after a starchiodide test for bromine was negative. To this solution at −45° C. was added amylene (8 ml.) and subsequently 19.14 gm. of 4'-nitrobenzyl 7-phenoxyacetamido-3-methylenecepham-4-carboxylate, 1-oxide. Comparative thin layer chromatography indicated that the reduction was complete after 20 minutes. The reaction mixture was allowed to warm to room temperature before it was concentrated in vacuo to about 40 ml. To the resulting solution was added 40 ml. of methanol. Crystals of the title product began to form within 30 seconds. Filtration provided 14.06 gm. (76.8%) of the title product; nmr data confirmed its structure.

(B) The same procedure was followed as described in paragraph A above except that the solution of the triphenyl phosphite-bromine complex was cooled to −60° C. before the addition of amylene and the 3-methylenecepham sulfoxide. The reaction was conducted at 40° to −45° C. Thin layer chromatography showed the reaction to be complete after 1 hour. A total of 14.06 gm. of the title product was isolated.

EXAMPLES 66–75

The following cephalosporin sulfoxides are reduced in accordance with the general procedure described in Example 1 using the indicated triaryl phosphite-halogen complex:

Example 66. Benzhydryl 7-formamido-3-acetoxymethylcephem-4-carboxylate 1-oxide; triphenyl phosphite-chlorine complex.

Example 67. 4'-Methoxybenzyl 7-[2-(2-thienyl)acetamido]-3-chloro-3-cephem-4-carboxylate 1-oxide; triphenyl phosphite-bromine complex.

Example 68. 2', 2', 2'-Trichloroethyl 7-chloroacetamido-3-bromomethyl-3-cephem-4-carboxylate 1-oxide; tri(p-methoxyphenyl)phosphite-chlorine complex.

Example 69. Benzyl 7-benzamido-3-methyl-3-cephem-4-carboxylate 1-oxide; triphenyl phosphite-chlorine complex.

Example 70. 4'-Nitrobenzyl 7-phenoxyacetamido-3-cephem-4-carboxylate 1-oxide; triphenyl phosphite-chlorine complex.

Example 71. t-Butyl 7-[2-(2-furyl)-2-methoxyiminoacetamido]-3-(1-methyl-1,2,3,4-tetrazol-5-yl)thiomethyl-3-cephem-4-carboxylate 1-oxide; triphenyl phosphite-chlorine complex.

Example 72. Benzhydryl 7-(2-formyloxy-2-phenylacetamido)-3-(1-methyl-1,2,3,4-tetrazol-5-yl)thiomethyl-3-cephem-4-carboxylate 1-oxide; tri(p-chlorophenyl)phosphite-chlorine complex.

Example 73. 4'-Nitrobenzyl 7-(4-nitrobenzyloxycarbonylamino)-3-methoxymethyl-3-cephem-4-carboxylate 1-oxide; tri(tolyl)phosphite-chlorine complex or triphenyl phosphite-bromine complex.

Example 74. 4'-Methoxybenzyl 7-phenylacetamido-3-acetylthiomethyl-3-cephem-4-carboxylate 1-oxide; triphenyl phosphite-chlorine complex.

Example 75. Benzhydryl 7-[2-(2-thienyl)acetamido]-3-methoxycarbonyl-3-cephem-4-carboxylate 1-oxide; tri(p-methoxyphenyl)phosphite-bromine complex.

EXAMPLES 76–85

In accordance with Scheme II in the foregoing specification the 7-acylamino cephalosporin sulfoxides used as starting materials in Examples 66–75 are coverted first to the corresponding cephalosporin imino halides and subsequently to the corresponding 7-amino cephalosporin esters using the triaryl phosphite-halogen complex indicated, pyridine as the base, and isobutanol, 1,2-propanediol or 1,3-propanediol for alcoholysis of the imino chloride.

EXAMPLE 86–95

In accordance with the general procedure described in Example 12 above the following designated 7-acylamino-3-hydroxy cephalosporin sulfoxide esters are converted to the corresponding 7-amino-3-chlorocephalosporin esters using the indicated reagents.

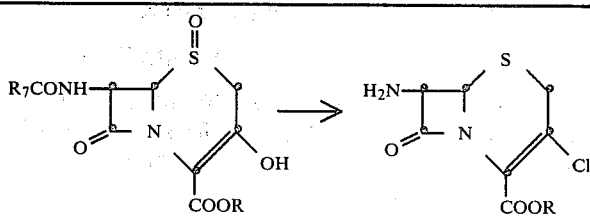

| Ex. | R | R | [Triaryl]phosphite | Solvent | Base | Alcohol |
|---|---|---|---|---|---|---|
| 86 | 4-nitrobenzyl | benzyl | triphenyl | $CH_2Cl_2$ | pyridine | isobutanol |
| 87 | benzhydryl | methyl | tritolyl | $CH_2ClCH_2Cl$ | quinoline | 1,2-propanediol |
| 88 | 2,2,2-trichloroethyl | hydrogen | triphenyl | $CHCl_2CHCl$ | triethylamine | 1,3-propanediol |
| 89 | 4-nitrobenzyl | 2-thienylmethyl | tri(4-chlorophenyl) | $CH_2Cl_2$ | diethylaniline | 2-methylbutanol |
| 90 | benzyl | benzyl | tri(4-methoxyphenyl) | $CH_2ClCH_2Cl$ | pyridine | 1,2-butanediol |
| 91 | pivaloyloxymethyl | phenoxymethyl | triphenyl | chlorobenzene | isoquinoline | isobutanol |
| 92 | tert-butyl | 4-chlorophenylthiomethyl | tritolyl | $CH_2Cl_2$ | DBU | 1,2-propanediol |
| 93 | 4-nitrobenzyl | α-formyloxybenzyl | triphenyl | $CH_2ClCH_2Cl$ | pyridine | 1,3-butanediol |
| 94 | phenacyl | phenoxymethyl | tri(4-methoxyphenyl) | $CHBr_2CH_2Cl$ | 2,6-lutidine | isobutanol |
| 95 | benzhydryl | α-benzhydryloxycarbonylbenzyl | triphenyl | $CH_2Cl_2$ | pyridine | isobutanol |

EXAMPLE 96

7-(2-Thienylacetamido)-3-methyl-3-cephem-4-carboxylic acid

A solution of triphenyl phosphite-chlorine complex in methylene chloride was prepared at −20° to −35° C. by addition of triphenyl phosphite (10 ml) to excess chlorine in methylene chloride (75 ml). Amylene (3ml) was used to quench excess chlorine.

To the triphenyl phosphite-chlorine complex solution (30 ml., 12.9 mmol) at 0° C. was added amylene (0.5 ml) and 7-(2-thienylacetamido)-3-methyl-3-cephem-4-carboxylic acid sulfoxide (0.90 gm, 2.2 mmol). The sulfoxide dissolved after 5 minutes at 0°–5° C. The reaction was stirred at 0°–5° C. for 25 minutes, during which time a precipitate formed. Water (0.1 ml) was added, and the mixture was stirred 5 minutes. After ether (50 ml) was added, the product was collected by filtration. After drying (45° C., 120 mm) for 2 days, 0.5 gm of the sulfide was obtained.

nmr (DMSO d-6) δ 8.21 (d, J=8 Hz, NH), 7.38 (m), 6.96 (d, J=4 Hz), 5.67 (d, d, J=5, 8 Hz, $H_7$), 4.81 (d, J=5 Hz, $H_6$), 3.82 (s), 3.60 (AB, $H_2$) 2.03 (s, methyl).

I claim:

1. A process for reducing a cephalosporin sulfoxide to the corresponding cephalosporin which comprises reacting said cephalosporin sulfoxide with about 1.0 to about 1.3 equivalents of a triaryl phosphite-halogen complex of the formula

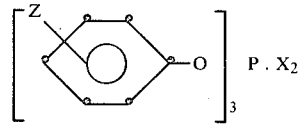

wherein X is Cl or Br, and Z is hydrogen, halo, $C_1$–$C_4$ alkyl or $C_1$–$C_4$ alkoxy, which is the kinetically controlled product of the reaction of equivalent amounts of a triaryl phosphite of the formula

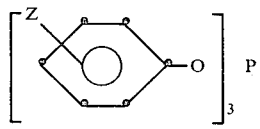

and chlorine or bromine in an inert organic solvent, in the presence of at least 1 equivalent of a halogen scavenger in a substantially anhydrous inert organic solvent at a temperature of about 30° C. or below; provided that when the cephalosporin sulfoxide has a free amino, hydroxy or carboxy group on the C-7 substituent, those groups are first protected by conventional amino, hydroxy or carboxy protecting groups.

2. The process of claim 1 wherein Z is hydrogen.
3. The process of claim 1 wherein X is Br.
4. The process of claim 1 wherein X is Cl.
5. A process for reducing a cephalosporin sulfoxide to the corresponding cephalosporin which comprises reacting said cephalosporin sulfoxide with about 1.0 to about 1.3 equivalents of a triphenyl phosphite-chlorine complex of the formula

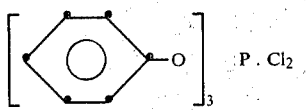

which
- (a) has a $^{31}P$ nuclear magnetic resonance signal in methylene chloride at $-3.7$ ppm relative to that of phosphoric acid;
- (b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
- (c) reacts with water to give HCl and triphenyl phosphate; and
- (d) reacts with n-butanol to give HCl, n-butyl chloride, and triphenyl phosphate;

in the presence of at least 1 equivalent of a halogen scavenger in a substantially anhydrous, inert organic solvent at a temperature of about 30° C. or below, provided that when the cephalosporin sulfoxide has a free amino, hydroxy or carboxy group on the C-7 substituent, those groups are first protected with conventional amino, hydroxy or carboxy protecting groups.

6. The process of claim 1 or claim 5 wherein the reaction temperature is about $-50°$ to about 30° C.

7. The process of claim 1 or claim 5 wherein the cephalosporin sulfoxide is a 3-cephem sulfoxide or a 3-exomethylenecepham sulfoxide.

8. The process of claim 7 wherein the halogen scavenger is a $C_2$–$C_{10}$ alkene, a cycloalkene having from 5 to 8 ring carbon atoms, a $C_4$–$C_8$ diene or a cyclodiene having from 5 to 8 ring carbon atoms, an alkyne having from 2 to 6 carbon atoms or a readily halogenated phenol derivative of the formula

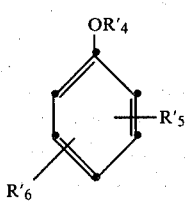

wherein $R_4'$ is $C_1$–$C_4$ alkyl, or $C_2$–$C_5$ alkanoyl, and $R_5'$ and $R_6'$ are independently hydrogen, $C_1$–$C_4$ alkoxy, $C_2$–$C_5$ alkanoyl or $C_1$–$C_4$ alkyl.

9. The process of claim 8 wherein the cephalosporin sulfoxide is a compound of the formula

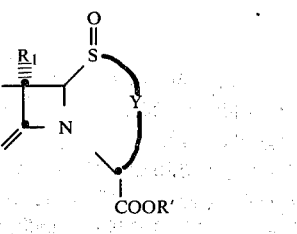

wherein
R' is hydrogen or a carboxylic acid protecting group;
$R_1$ is hydrogen or methoxy;

is amino protected by a conventional amino protecting group; or
$R_2$ is hydrogen or an acyl group derived from a carboxylic acid, and
$R_3$ is an acyl group derived from a carboxylic acid; or
$R_2$ and $R_3$ taken together with the nitrogen atom to which they are attached form a group of the formula

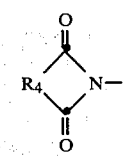

wherein
$R_4$ is the residue of an acyl group derived from a dicarboxylic acid; and Y is a divalent radical selected from the group consisting of

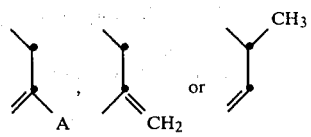

wherein
A is hydrogen, chloro, bromo, hydroxy, protected hydroxy, $C_1$–$C_4$ alkoxy, methyl, $C_1$–$C_4$ alkanesulfonyloxy, $C_1$–$C_4$ alkylphenylsulfonyloxy, or a group of the formula —$CH_2B$ wherein
B is
 (1) $C_2$–$C_4$ alkanoyl, carbamoyloxy, or $C_1$–$C_4$ alkylcarbamoyloxy;
 (2) $C_1$–$C_4$ alkoxy;
 (3) chloro or bromo;
 (4) $C_1$–$C_4$ alkoxycarbonyl or ($C_2$–$C_6$ haloalkoxy)carbonyl; or
 (5) a group of the formula -$SR_9$ wherein $R_9$ is
  (a) $C_1$–$C_4$ alkanoyl;
  (b) $C_1$–$C_4$ alkyl, phenyl or phenyl substituted with 1 or 2 substituents selected from the group consisting of $C_1$–$C_4$ alkyl, $C_1$–$C_4$ alkoxy, protected hydroxy, chloro, bromo, fluoro, nitro, cyano, methanesulfonamido and trifluoromethyl; or
  (c) a 5- or 6-membered heterocyclic ring containing 1 to 4 heteroatoms selected from the group consisting of oxygen, sulfur and nitrogen, said ring being unsubstituted or substituted by $C_1$–$C_4$ alkyl, $C_1$–$C_4$ alkoxy, chloro, bromo, oxo, halo($C_1$–$C_4$ alkyl), protected amino, protected amino($C_1$–$C_4$ alkyl), protected hydroxy, protected hydroxy($C_1$–$C_4$ alkyl), protected carboxy, or protected carboxy($C_1$–$C_4$)alkyl.

10. The process of claim 9 wherein R' is a carboxylic acid protecting group.

11. The process of claim 10 wherein $R_1$ is hydrogen.

12. The process of claim 11 wherein $R_2$ is hydrogen and $R_3$ is and acyl group of the formula $R_7CO-$ wherein $R_7$ is (1) hydrogen, $C_1-C_6$ alkyl, halo($C_1-C_4$)-alkyl, cyanomethyl, trifluoromethylthiomethyl, or 4-protected amino-4-protected carboxybutyl;

(2) the group $R_a$ wherein $R_a$ is phenyl or phenyl substituted with 1 or 2 substituents selected from the group consisting of $C_1-C_4$ alkyl, $C_1-C_4$ alkoxy, protected hydroxy, chloro, bromo, fluoro, iodo, nitro, cyano, carbamyl, methanesulfonamido and trifluoromethyl;

(3) an arylalkyl group of the formula $$R^o\text{-}(Q)_m\text{-}CQ_1Q_2\text{-}$$

wherein $R^o$ is $R_a$ as defined above, 1,4-cyclohexadienyl, or a 5-membered heterocyclic ring containing 1 to 4 heteroatoms selected from the group consisting of oxygen, nitrogen, and sulfur, said ring being unsubstituted or substituted by $C_1-C_4$ alkyl, $C_1-C_4$ alkoxy, chloro, bromo, oxo, protected amino, protected amino ($C_1-C_4$ alkyl), protected hydroxy or protected carboxy;

m is 1 or 0;

Q is oxygen or sulfur, and $Q_1$ and $Q_2$ are independently hydrogen or methyl; subject to the limitation that in the above formula when m is 1, $R^o$ is limited to $R_a$;

(4) a substituted arylalkyl group of the formula

wherein $R^o$ is as defined above and W is ureido, protected amino, protected hydroxy or protected carboxy; or (5) a substituted oximino group of the formula

wherein $R^o$ is defined as in paragraph (3) immediately hereinabove and $R_b$ is $C_1-C_4$ alkoxy.

13. The process of claim 12 wherein Y is a radical of the formula

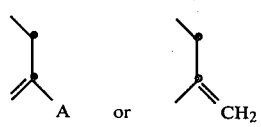

14. The process of claim 13 wherein the halogen scavenger is a $C_2-C_6$ alkene.

15. The process of claim 14 wherein the temperature is about $-50°$ to about $30°$ C.

16. The process of claim 15 wherein the inert organic solvent is a halogenated hydrocarbon.

17. The process of claim 16 wherein A is methyl or chloro and $R_3$ is phenoxymethyl, benzyl or 2-thienylmethyl.

18. A process for preparing a compound of the formula

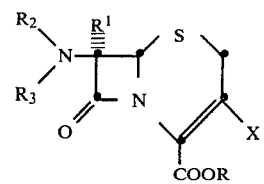

by reacting a compound of the formula

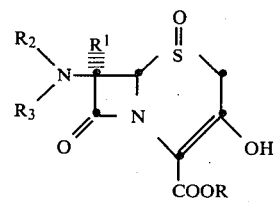

with about 2 to about 3 equivalents of a triaryl phosphite-halogen complex of the formula

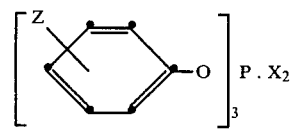

wherein X is Cl or Br, and Z is hydrogen, halo, $C_1-C_4$ alkyl or $C_1-C_4$ alkoxy, which is the kinetically controlled product of the reaction of equivalent amounts of a triaryl phosphite of the formula

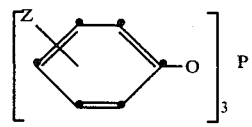

and chlorine or bromine in an inert organic solvent, in the presence of at least 1 molar equivalent of a halogen scavenger in a substantially anhydrous inert organic solvent at a temperature below about $30°$ C.; wherein in the above formulas R is a carboxylic acid protecting group;

$R_1$ is hydrogen or methoxy;

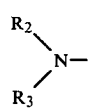

is amino protected by a conventional amino protecting group; or $R_2$ is hydrogen or an acyl group derived from a carboxylic acid, and $R_3$ is an acyl group derived from a carboxylic acid; or $R_2$ and $R_3$ taken together with the nitrogen atom to which they are attached form a group of the formula

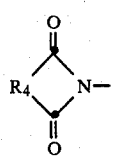

wherein
R₄ is the residue of an acyl group derived from a dicarboxylic acid;
provided that when the C-7 substituent

on the cephalosporin sulfoxide is substituted by hydroxy, amino or carboxy groups, those groups are first protected by conventional hydroxy, amino, or carboxy protecting groups.

19. The process of claim 18 wherein Z is hydrogen.
20. The process of claim 18 wherein X is Br.
21. The process of claim 18 wherein X is Cl.
22. A process for preparing a compound of the formula

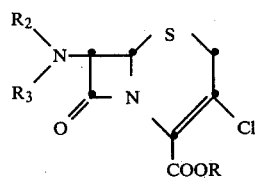

by reacting a compound of the formula

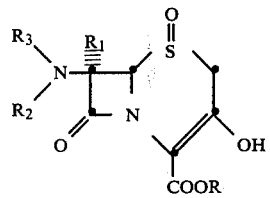

with about 2 to about 3 equivalent of a triphenyl phosphite-chlorine complex of the formula

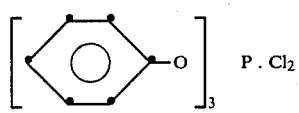

which
(a) has a ³¹P nuclear magnetic resonance signal in methylene chloride at −3.7 ppm relative to that of phosphoric acid;
(b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;

in the presence of at least 1 molar equivalent of a halogen scavenger in a substantially anhydrous inert organic solvent at a temperature of about 30° C. below; wherein in the above formulas R is a carboxylic acid protecting group;
R₁ is hydrogen or methoxy; and

is amino protected by a conventional amino protecting group; or
R₂ is hydrogen or an acyl group derived from a carboxylic acid, and
R₃ is an acyl group derived from a carboxylic acid; or
R₂ and R₃ taken together with the nitrogen atom to which they are attached form a group of the formula

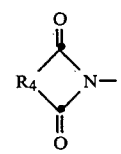

wherein
R₄ is the residue of an acyl group derived from a dicarboxylic acid, provided that when the C-7 substituent

on the cephalosporin sulfoxide is substituted by hydroxy, amino or carboxy groups, those groups are first protected by conventional hydroxy, amino, or carboxy protecting groups.

23. The process of claim 18 or claim 19 or claim 22 wherein the temperature is about −50° to about 30° C.

24. The process of claim 23 wherein, additionally, the process is conducted in the presence of about 1 to about 2 equivalents of a tertiary amine base.

25. The process of claim 24 wherein R₁ is hydrogen.

26. The process of claim 25 wherein R₂ is hydrogen and R₃ is an acyl group derived from a C₁–C₂₀ carboxylic acid.

27. The process of claim 25 wherein the halogen scavenger is a C₂–C₁₀ alkene, a cycloalkene having from 5 to 8 ring carbon atoms, a C₄–C₈ diene or a cyclodiene having from 5 to 8 ring carbon atoms, an alkyne having from 2 to 6 carbon atoms or a readily halogenated phenol derivative of the formula

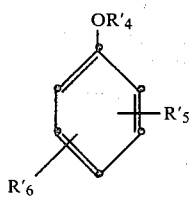

wherein $R_4'$ is $C_1-C_4$ alkyl, or $C_2-C_5$ alkanoyl, and $R_5'$ and $R_6'$ are independently hydrogen, $C_1-C_4$ alkoxy, $C_2-C_5$ alkanoyl or $C_1-C_4$ alkyl.

28. The process of claim 27 wherein the halogen scavenger is a $C_2-C_6$ alkene.

29. A process for preparing a cephalosporing imino halide of the formula

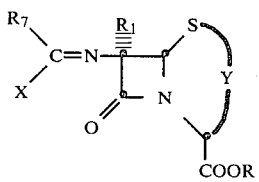

which comprises reacting a 7-acylamino cephalosporin sulfoxide of the formula

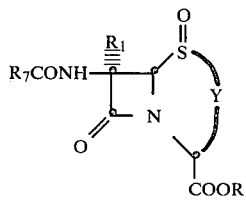

with about 2 to about 3 equivalents of a triaryl phosphite-halogen complex of the formula

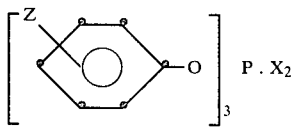

wherein X is Cl or Br, and Z is hydrogen, halo, $C_1-C_4$ alkyl or $C_1-C_4$ alkoxy, which is the kinetically controlled product of the reaction of equivalent amounts of a triaryl phosphite of the formula

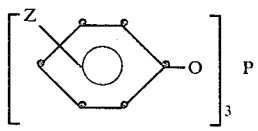

and chlorine or bromine in an inert organic solvent, in the presence of at least 1 equivalent of a halogen scavenger and about 1 to about 2 equivalents of a tertiary amine base in a substantially anhydrous inert organic solvent at a temperature of about 30° C. or below, wherein in the above formulas R is a carboxylic acid protecting group;
$R_1$ is hydrogen or methoxy;

$R_7$ is the residue of an acyl group derived from a $C_1-C_{20}$ carboxylic acid of the formula $R_7COOH$; and Y is a divalent radical selected from the group consisting of

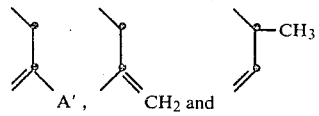

wherein A' is hydrogen, chloro, bromo, protected hydroxy, $C_1-C_4$ alkoxy, methyl, $C_1-C_4$ alkanesulfonyloxy, $C_1-C_4$ alkylphenylsulfonyloxy, or a group of the formula $-CH_2B$ wherein B is (1) $C_2-C_4$ alkanoyl, carbamoyloxy, or $C_1-C_4$ alkylcarbamoyloxy;
(2) $C_1-C_4$ alkoxy;
(3) chloro or bromo;
(4) $C_1-C_4$ alkoxycarbonyl or ($C_2-C_6$ haloalkoxy)-carbonyl; or
(5) a group of the formula $-SR_9$ wherein $R_9$ is
(a) $C_1-C_4$ alkanoyl;
(b) $C_1-C_4$ alkyl, phenyl or phenyl substituted with 1 or 2 substituents selected from the group consisting of $C_1-C_4$ alkyl, $C_1-C_4$ alkoxy, protected hydroxy, chloro, bromo, fluoro, nitro, cyano, methanesulfonamido and trifluoromethyl; or
(c) a 5- or 6-membered heterocyclic ring containing 1 to 4 heteroatoms selected from the group consisting of oxygen, sulfur and nitrogen, said ring being unsubstituted or substituted by $C_1-C_4$ alkyl, $C_1-C_4$ alkoxy, chloro, bromo, oxo, halo($C_1-C_4$ alkyl), protected amino, protected amino($C_1-C_4$ alkyl), protected hydroxy, protected hydroxy($C_1-C_4$ alkyl), protected carboxy, or protected carboxy ($C_1-C_4$ alkyl); provided that when $R_7$ is substituted by hydroxy, amino or carboxy groups, those groups are first protected by conventional hydroxy, amino, or carboxy protecting groups.

30. The process of claim 29 wherein Z is hydrogen.
31. The process of claim 29 wherein X is Br.
32. The process of claim 29 wherein X is Cl.
33. The process of claim 29 wherein $R_1$ is hydrogen.
34. The process of claim 33 wherein Y is a radical of the formula

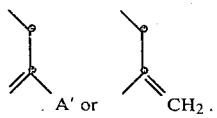

35. The process of claim 29 wherein $R_1$ is methoxy.
36. A process for preparing a cephalosporin imino chloride of the formula

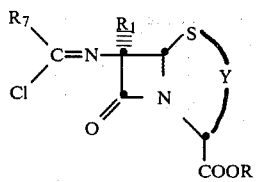

which comprises reacting a 7-acylamino cephalosporin sulfoxide of the formula

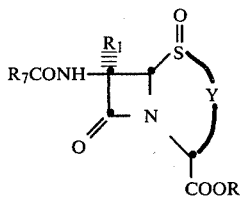

with about 2 to about 3 equivalents of a triphenyl phosphite-chlorine complex of the formula

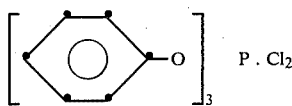

which
(a) has a $^{31}$P nuclear magnetic resonance signal in methylene chloride at $-3.7$ ppm relative to that of phosphoric acid;
(b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;

in the presence of at least 1 equivalent of a halogen scavenger and about 1 to about 2 equivalents of a tertiary amine base in a substantially anhydrous inert organic solvent at a temperature of about 30° C. or below, wherein in the above formulas R is a carboxylic acid protecting group;
$R_1$ is hydrogen or methoxy;
$R_7$ is the residue of an acyl group derived from a $C_1$–$C_{20}$ carboxylic acid of the formula $R_7COOH$; and
Y is a divalent radical selected from the group consisting of

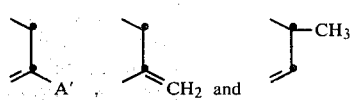

wherein A' is hydrogen, chloro, bromo, protected hydroxy, $C_1$–$C_4$ alkoxy, methyl, $C_1$–$C_4$ alkanesulfonyloxy, $C_1$–$C_4$ alkylphenylsulfonyloxy, or a group of the formula -CH$_2$B wherein B is (1) $C_2$–$C_4$ alkanoyl, carbamoyloxy, or $C_1$–$C_4$ alkylcarbamoyloxy;
(2) $C_1$–$C_4$ alkoxy;
(3) chloro or bromo;
(4) $C_1$–$C_4$ alkoxycarbonyl or ($C_2$–$C_6$ haloalkyl)-carbonyl; or
(5) a group of the formula -SR$_9$ wherein R$_9$ is
(a) $C_1$–$C_4$ alkanoyl;
(b) $C_1$–$C_4$ alkyl, phenyl or phenyl substituted with 1 or 2 substituents selected from the group consisting of $C_1$–$C_4$ alkyl, $C_1$–$C_4$ alkoxy, protected hydroxy, chloro, bromo, fluoro, nitro, cyano, methanesulfonamido and trifluoromethyl; or
(c) a 5- or 6-membered heterocyclic ring containing 1 to 4 heteroatoms selected from the group consisting of oxygen, sulfur and nitrogen, said ring being unsubstituted or substituted by $C_1$–$C_4$ alkyl, $C_1$–$C_4$ alkoxy, chloro, bromo, oxo, halo($C_1$–$C_4$ alkyl), protected amino, protected amino($C_1$–$C_4$ alkyl), protected hydroxy, protected hydroxy($C_1$–$C_4$ alkyl), protected carboxy, or protected carboxy($C_1$–$C_4$ alkyl);

provided that when R$_7$ is substituted by hydroxy, amino or carboxy groups, those groups are first protected by conventional hydroxy, amino, or carboxy protecting groups.

37. The process of claim 36 wherein Y is a radical of the formula

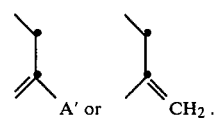

38. The process of claim 36 wherein R$_1$ is hydrogen.
39. The process of claim 36 wherein R$_1$ is methoxy.
40. A process for preparing a 3-halocephalosporin imino halide of the formula

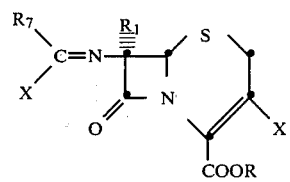

which comprises reacting a 7-acylamino-3-hydroxycephalosporin sulfoxide of the formula

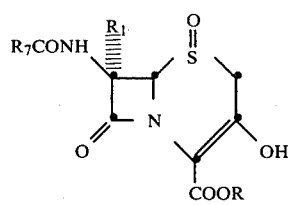

with about 3 to about 5 equivalents of a triaryl phosphite-halogen complex of the formula

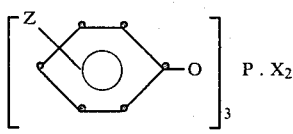

wherein X is Cl or Br, and Z is hydrogen, halo, $C_1$–$C_4$ alkyl or $C_1$–$C_4$ alkoxy, which is the kinetically controlled product of the reaction of equivalent amounts of a triaryl phosphite of the formula

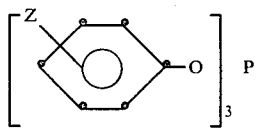

and chlorine or bromine in an inert organic solvent, in the presence of at least 1 equivalent of a halogen scavenger and about 2.0 to about 5.0 equivalents of a tertiary amine base in a substantially anhydrous inert organic solvent at a temperature of about 30° or below; wherein in the above formulas R is a carboxylic acid protecting group;
$R_1$ is hydrogen or methoxy;
X is Cl or Br; and
$R_7$ is the residue of an acyl group derived from a $C_1$–$C_{20}$ carboxylic acid of the formula $R_7COOH$;

provided that when $R_7$ is substituted by hydroxy, amino or carboxy groups, those groups are first protected by conventional hydroxy, amino, or carboxy protecting groups.

41. The process of claim 40 wherein Z is hydrogen.
42. The process of claim 40 wherein X is Br.
43. The process of claim 40 wherein X is Cl.
44. A process for preparing a 3-chlorocephalosporin imino chloride of the formula

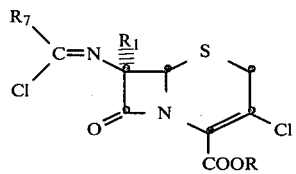

which comprises reacting a 7-acylamino-3-hydroxycephalosporin sulfoxide of the formula

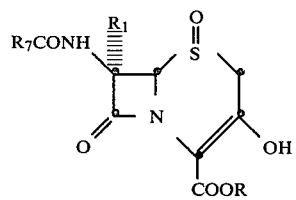

with about 3 to about 5 equivalents of a triphenyl phosphite-chlorine complex of the formula

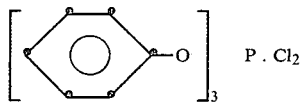

which
(a) has a $^{31}P$ nuclear magnetic resonance signal in methylene chloride at −3.7 ppm relative to that of phosphoric acid;
(b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;

in the presence of at least 1 equivalent of a halogen scavenger and about 2.0 to about 5.0 equivalents of a tertiary amine base in a substantially anhydrous inert organic solvent at a temperature of about 30° C. or below; wherein in the above formulas R is a carboxylic acid protecting group;
$R_1$ is hydrogen or methoxy; and
$R_7$ is the residue of an acyl group derived from a $C_1$–$C_{20}$ carboxylic acid of the formula $R_7COOH$;

provided that when $R_7$ is substituted by hydroxy, amino or carboxy groups, those groups are first protected by conventional hydroxy, amino, or carboxy protecting groups.

45. The process of claim 44 wherein $R_1$ is hydrogen.
46. The process of claim 29, claim 36, claim 40, or claim 44 wherein the temperature is about −50° to about 30° C.
47. The process of claim 46 wherein the C-7 acylamino group of the 3-hydroxy cephalosporin sulfoxide is a conventional penicillin or cephalosporin acylamino group.
48. The process of claim 46 wherein $R_7$ is
(1) hydrogen, $C_1$–$C_6$ alkyl, halo($C_1$–$C_4$)alkyl, cyanomethyl, trifluoromethylthiomethyl, or 4-protected amino-4-protected carboxybutyl;
(2) the group $R_a$ wherein $R_a$ is phenyl or phenyl substituted with 1 or 2 substituents selected from the group consisting of $C_1$–$C_4$ alkyl, $C_1$–$C_4$ alkoxy, protected hydroxy, chloro, bromo, fluoro, iodo, nitro, cyano, carbamyl, methanesulfonamido and trifluoromethyl;
(3) an arylalkyl group of the formula $R^o$-(Q)$_m$-CQ$_1$Q$_2$- wherein $R^o$ is $R_a$ as defined above, 1,4-cyclohexadienyl, or a 5-membered heterocyclic ring containing 1 to 4 heteroatoms selected from the group consisting of oxygen, nitrogen, and sulfur, said ring being unsubstituted or substituted by $C_1$–$C_4$ alkyl, $C_1$–$C_4$ alkoxy, chloro, bromo, oxo, protected amino, protected amino($C_1$–$C_4$ alkyl), protected hydroxy or protected carboxy;
m is 1 or 0;
Q is oxygen or sulfur, and
$Q_1$ and $Q_2$ are independently hydrogen or methyl;

subject to the limitation that in the above formula when m is 1, $R^o$ is limited to $R_a$;

(4) a substituted arylalkyl group of the formula

wherein $R^o$ is as defined above and W is ureido, protected amino, protected hydroxy or protected carboxy; or (5) a substituted oximino group of the formula

wherein $R^o$ is defined as in paragraph (3) immediately hereinabove and $R_b$ is $C_1$–$C_4$ alkoxy.

49. The process of claim 48 wherein the halogen scavenger is a $C_2$–$C_{10}$ alkene, a cycloalkene having from 5 to 8 ring carbon atoms, a $C_4$–$C_8$ diene or a cyclodiene having from 5 to 8 ring carbon atoms, an alkyne having from 2 to 6 carbon atoms or a readily halogenated phenol derivative of the formula

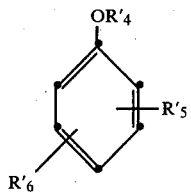

wherein $R_4'$ is $C_1$–$C_4$ alkyl, or $C_2$–$C_5$ alkanoyl, and $R_5'$ and $R_6'$ are independently hydrogen, $C_1$–$C_4$ alkoxy, $C_2$–$C_5$ alkanoyl or $C_1$–$C_4$ alkyl.

50. The process of claim 49 wherein the tertiary amine base has a $pK_b$ value of about 6 to about 10.

51. The process of claim 50 wherein the temperature is about −30° to about 0° C.

52. The process of claim 51 wherein the halogen scavenger is a $C_2$–$C_6$ alkene.

53. The process of claim 52 wherein $R_1$ is hydrogen, $R_7$ is a group of the formula $R^o$-$(Q)_m$-$CQ_1Q_2$- wherein $R^o$ is 2-thienyl, phenyl or substituted phenyl, Q is 0, m is 1 or 0, and $Q_1$ and $Q_2$ are hydrogen.

54. The process of claim 50 wherein about 4 to about 5 equivalents of a triaryl phosphite-halogen complex and about 3.5 to about 4 equivalents of a tertiary amine base are employed.

55. The process of claim 54 wherein the triaryl phosphite-halogen complex is stabilized with a tertiary amine base.

56. The process of claim 54 wherein after formation of the cephalosporin imino halide is complete, an excess of a $C_1$–$C_{15}$ aliphatic alcohol and hydrogen chloride are added to the reaction mixture to provide the corresponding 7-amino cephalosporin.

57. The process of claim 56 wherein about 3 to about 15 equivalents of a $C_4$–$C_{12}$ β-disubstituted primary aliphatic alcohol, a $C_2$–$C_{12}$ 1,2-diol, or a $C_3$–$C_{15}$ 1,3-diol are added to the reaction mixture to provide a 7-amino cephalosporin of the formula

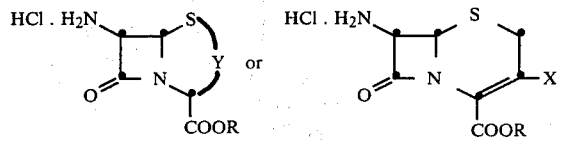

58. The process of claim 57 wherein the alcohol employed is isobutanol, 1,3-propanediol or 1,2-propanediol.

59. The process of claim 58 wherein the inert organic solvent is a hydrogenated hydrocarbon solvent.

60. The process of claim 43 or claim 44 wherein the temperature is about −50° to about 0° C.

61. The process of claim 60 wherein the halogen scavenger is a $C_2$–$C_{10}$ alkene, a cycloalkene having from 5 to 8 ring carbon atoms, a $C_4$–$C_8$ diene or a cyclodiene having from 5 to 8 ring carbon atoms, an alkyne having from 2 to 6 carbon atoms or a readily halogenated phenol derivative of the formula

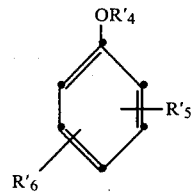

wherein $R_4'$ is $C_1$–$C_4$ alkyl, or $C_2$–$C_5$ alkanoyl, and $R_5'$ and $R_6'$ are independently hydrogen $C_1$–$C_4$ alkoxy, $C_2$–$C_5$ alkanoyl or $C_1$–$C_4$ alkyl.

62. The process of claim 61 wherein the tertiary amine base has a $pK_b$ of about 6 to about 10.

63. The process of claim 62 wherein $R_1$ is hydrogen.

64. The process of claim 63 wherein the C-7 acylamino group of the 3-hydroxy cephalosporin sulfoxide is a conventional penicillin or cephalosporin acylamino group.

65. The process of claim 64 wherein about 4 to about 5 equivalents of triaryl phosphite-chlorine complex and about 3.5 to about 4.0 equivalents of a tertiary amine base are employed.

66. The process of claim 65 wherein after the formation of the 3-chloro cephalosporin imino chloride is complete, an excess of a $C_1$–$C_{15}$ aliphatic alcohol and hydrogen chloride are added to the reaction mixture to provide the corresponding 7-amino 3-chloro cephalosporin ester of the formula

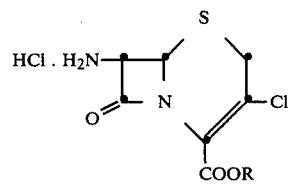

67. The process of claim 66 wherein about 3 to about 15 equivalents of a $C_4$–$C_{12}$ β-disubstituted primary aliphatic alcohol, a $C_2$–$C_{12}$ 1,2-diol or a $C_3$–$C_{15}$ 1,3-diol are added to the reaction mixture.

68. The process of claim 67 wherein the temperature is about −30° to about 0° C.

69. The process of claim 68 wherein Z=hydrogen.

70. The process of claim 69 wherein the alcohol or diol is isobutanol, 1,2-propanediol, or 1,3-propanediol.

71. The process of claim 70 wherein $R_7$ is a group of the formula $R^o\text{-}(O)_m\text{-}Ch_2\text{-}$ wherein $R^o$ is 2-thienyl, phenyl or substituted phenyl and m is 1 or 0.

72. The process of claim 71 wherein the triphenyl phosphite-chlorine complex is stabilized with a tertiary amine base.

73. The process of claim 72 wherein the tertiary amine base is pyridine.

74. The process of claim 73 wherein R is 4-nitrobenzyl.

75. The process of claim 74 wherein $R_7$ is 2-thienylmethyl, phenoxymethyl or benzyl.

76. The process of claim 75 wherein the inert organic solvent is methylene chloride.

77. The process of claim 76 wherein about 4.4 equivalents of triphenyl phosphite-chlorine complex and about 3.8 equivalents of pyridine are employed.

* * * * *

UNITED STATES PATENT AND TRADEMARK OFFICE
CERTIFICATE OF CORRECTION

PATENT NO. : 4,223,133  
DATED : September 16, 1980  
INVENTOR(S) : Charles A. Bunnell Page 1 of 3

It is certified that error appears in the above-identified patent and that said Letters Patent are hereby corrected as shown below:

Column 3, line 20, "which in" should read --which is--.

Column 13, line 56, "4ben-" should read -- 4-ben- --.

Column 15, line 22, "E. Halsam" should read --E. Haslam--.

Column 17, lines 2-10, "

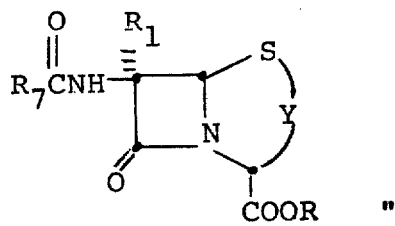

"

should read --

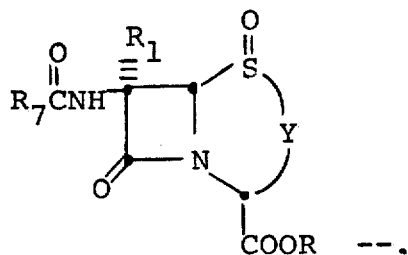

--.

UNITED STATES PATENT AND TRADEMARK OFFICE
CERTIFICATE OF CORRECTION

PATENT NO. : 4,223,133

Page 2 of 3

DATED : September 16, 1980

INVENTOR(S) : Charles A. Bunnell

It is certified that error appears in the above-identified patent and that said Letters Patent are hereby corrected as shown below:

Column 26, line 66 (under Pyridine (ml/equiv) heading, "12.2/3.8" should read -- 12.3/3.8 --.

Column 30, line 54, "are coverted" should read --are converted --.

Column 37, lines 27-35, "

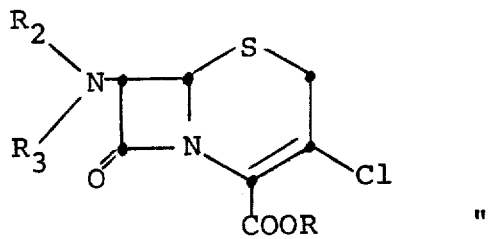

"

should read --

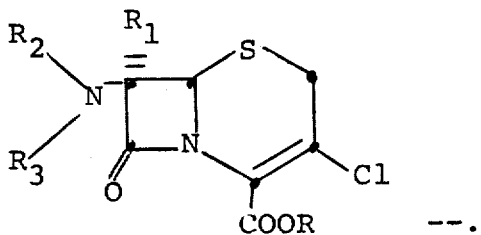

--.

UNITED STATES PATENT AND TRADEMARK OFFICE
CERTIFICATE OF CORRECTION

PATENT NO. : 4,223,133

DATED : September 16, 1980

INVENTOR(S) : Charles A. Bunnell

It is certified that error appears in the above-identified patent and that said Letters Patent are hereby corrected as shown below:

Column 38, line 5, "30°C. below" should read -- 30°C. or below --.

Column 39, line 15, "cephalosporing imino" should read --cephalosporin imino--.

Column 47, line 4, "$R^{\circ}-(O)_m-Ch_2-$" should read -- $R^{\circ}-(O)_m-CH_2-$ --.

Signed and Sealed this

Thirtieth Day of June 1981

[SEAL]

Attest:

RENE D. TEGTMEYER

Attesting Officer

Acting Commissioner of Patents and Trademarks